(12) United States Patent
An et al.

(10) Patent No.: US 8,067,002 B2
(45) Date of Patent: Nov. 29, 2011

(54) HUMANIZED ANTI-FACTOR D ANTIBODIES

(75) Inventors: Ling-Ling An, Boyds, MD (US); Sek Chung Fung, Houston, TX (US); Robert F. Kelley, San Bruno, CA (US); Henry B. Lowman, El Granada, CA (US); Sanjaya Singh, Sandy Hook, CT (US); Herren Wu, Boyds, MD (US)

(73) Assignee: Genentech, Inc., South San Francisco, CA (US)

( * ) Notice: Subject to any disclaimer, the term of this patent is extended or adjusted under 35 U.S.C. 154(b) by 692 days.

(21) Appl. No.: 11/931,060

(22) Filed: Oct. 31, 2007

(65) Prior Publication Data

US 2008/0118506 A1    May 22, 2008

Related U.S. Application Data

(60) Provisional application No. 60/856,505, filed on Nov. 2, 2006.

(51) Int. Cl.
*A61K 39/395* (2006.01)
*C07K 16/36* (2006.01)

(52) U.S. Cl. .......... 424/145.1; 424/130.1; 424/133.1; 424/141.1; 424/152.1; 424/158.1; 530/387.1; 530/387.3; 530/388.1; 530/388.2; 530/388.25

(58) Field of Classification Search .......... None
See application file for complete search history.

(56) References Cited

U.S. PATENT DOCUMENTS

| | | | |
|---|---|---|---|
| 4,816,567 A | 3/1989 | Cabilly | |
| 5,456,909 A | 10/1995 | Marsh et al. | |
| 5,534,615 A | 7/1996 | Baker et al. | |
| 5,624,837 A | 4/1997 | Fodor et al. | |
| 5,627,264 A | 5/1997 | Fodor et al. | |
| 5,679,546 A | 10/1997 | Ko et al. | |
| 5,679,564 A | 10/1997 | Pace et al. | |
| 5,851,528 A | 12/1998 | Ko et al. | |
| 5,853,722 A | 12/1998 | Rollins et al. | |
| 5,856,297 A | 1/1999 | Fearon et al. | |
| 5,856,300 A | 1/1999 | Rittershaus et al. | |
| 5,858,969 A | 1/1999 | Marsh et al. | |
| 5,861,156 A | 1/1999 | George et al. | |
| 6,333,034 B1 | 12/2001 | Gupta-Bansal et al. | |
| 6,410,708 B1 | 6/2002 | Ashkenazi et al. | |
| 6,472,520 B2 | 10/2002 | Fisher | |
| 6,534,058 B2 | 3/2003 | Fung | |
| 6,569,992 B1 | 5/2003 | LaFleur et al. | |
| 6,642,353 B1 | 11/2003 | McConnell et al. | |
| 6,838,554 B2 | 1/2005 | Ashkenazi et al. | |
| 6,956,107 B2 | 10/2005 | Fung et al. | |
| 7,112,327 B2 | 9/2006 | Fung | |
| 7,192,589 B2 | 3/2007 | Ashkenazi et al. |
| 7,211,400 B2 | 5/2007 | Ashkenazi et al. |
| 7,419,663 B2 | 9/2008 | Ashkenazi et al. |
| 7,439,331 B2 | 10/2008 | Fung |
| 7,282,565 B2 | 8/2010 | Goddard et al. |
| 2003/0129187 A1 | 7/2003 | Fung et al. |
| 2003/0207309 A1 | 11/2003 | Hageman et al. |
| 2004/0152105 A1 | 8/2004 | Vogt et al. |
| 2005/0191298 A1 | 9/2005 | Bell et al. |
| 2005/0197285 A1 | 9/2005 | Rosen et al. |
| 2005/0222027 A1 | 10/2005 | Chiang et al. |
| 2006/0067935 A1 | 3/2006 | Ambati |
| 2006/0233803 A1 | 10/2006 | Ashkenazi et al. |
| 2007/0190054 A1 | 8/2007 | Ashkenazi et al. |
| 2008/0193442 A1 | 8/2008 | Fung et al. |
| 2009/0181017 A1 | 7/2009 | Hass et al. |
| 2009/0214538 A1 | 8/2009 | Fung et al. |
| 2009/0269338 A1 | 10/2009 | Huang et al. |
| 2011/0123528 A1 | 5/2011 | An et al. |

FOREIGN PATENT DOCUMENTS

| | | |
|---|---|---|
| EP | 0 239 400 | 3/1994 |
| WO | 95/29697 | 11/1995 |
| WO | WO 99/27098 | 3/1999 |
| WO | WO 99/40100 | 8/1999 |
| WO | WO 99/42133 | 8/1999 |
| WO | WO 99/46281 | 9/1999 |
| WO | WO 00/12703 | 3/2000 |
| WO | WO 00/036102 | 6/2000 |
| WO | WO 00/37638 | 6/2000 |
| WO | WO 00/42072 | 7/2000 |
| WO | WO 00/53749 | 9/2000 |
| WO | WO 00/53758 | 9/2000 |
| WO | WO 01/04311 | 1/2001 |
| WO | WO 01/36432 | 5/2001 |
| WO | WO 01/40466 | 6/2001 |
| WO | WO 02/00690 | 1/2002 |
| WO | WO 02/08284 | 1/2002 |
| WO | WO 02/30985 | 4/2002 |
| WO | WO 2004/014953 | 2/2004 |
| WO | WO 2004/022594 | 3/2004 |

(Continued)

OTHER PUBLICATIONS

Carter et al., "Humanization of an anti-p185HER2 antibody for human cancer therapy". Proc. Natl. Acad. Sci. USA, 89:4285-4289 (1992).

(Continued)

*Primary Examiner* — Phillip Gambel
(74) *Attorney, Agent, or Firm* — Jones Day

(57) ABSTRACT

The invention relates to humanized anti-human Factor D monoclonal antibodies, their nucleic acid and amino acid sequences, the cells and vectors that harbor these antibodies and their use in the preparation of compositions and medicaments for treatment of diseases and disorders associated with excessive or uncontrolled complement activation. These antibodies are useful for diagnostics, prophylaxis and treatment of disease.

28 Claims, 11 Drawing Sheets

FOREIGN PATENT DOCUMENTS

| | | |
|---|---|---|
| WO | WO 2005/025509 | 3/2005 |
| WO | WO 2005/102387 | 11/2005 |
| WO | WO 2006/042329 | 4/2006 |
| WO | WO 2006/062716 | 6/2006 |
| WO | WO 2006/071856 | 7/2006 |
| WO | WO 2006/088950 | 8/2006 |
| WO | WO 2007/044668 | 4/2007 |
| WO | WO 2007/053447 | 5/2007 |
| WO | WO 2007/56227 | 5/2007 |
| WO | WO 2007/087384 | 8/2007 |
| WO | WO 2008/055206 | 5/2008 |
| WO | WO 2008/147883 | 12/2008 |
| WO | WO 2009/134711 | 11/2009 |

OTHER PUBLICATIONS

Chothia et al., "Canonical structures for the hypervariable regions of immunoglobulins." J. Mol. Biol., 196:901-917 (1987).

Evans et al., "Rapid Expression of an Anti-Human C5 Chimeric Fab Utilizing a Vector that Replicates in COS and 293 Cells," J. Immunol., 184: 123-138 (1995).

Hakimi et al., "Reduced immunogenicity and improved pharmacokinetics of humanized anti-Tac in cynomolgus monkeys". J. Immunol., 147(4):1352-1959 (1991).

Harboe et al., "The quantitative role of alternative pathway amplification in classical pathway induced terminal complement activation." Clinical and Experimental Immunology, 138(3):439-446 (2004).

Haubenwallner et al., "A novel missense mutation in the gene for lipoprotein lipase resulting in a highly conservative amino acid substitution ($Asp^{180} \rightarrow Glu$) causes familial chylomicronemia (type I hyperlipoproteinemia)" Genomics, 18(2):392-396 (1993).

Huber-Lang et al., "Role of C5a in Multiorgan Failure During Sepsis" J. of Immunology, 166:1193-1198 (2001).

Jaffers et al., "Monoclonal antibody therapy. Anti-idiotypic and non-anti-idiotypic antibodies to OKT3 arising despite intense immunosuppression". Transplantation 41(5):572-578 (1986).

Jones et al., "Replacing the complementarity-determining regions in a human antibody with those from a mouse." Nature, 321:522-525 (1986).

Junghans et al., "Anti-Tac-H, a humanized antibody to the interleukin 2 receptor with new features for immunotherapy in malignant and immune disorders". Cancer Res. 50:1495-1502 (1990).

Khazaeli et al., "Phase I trial of multiple large doses of murine monoclonal antibody CO17-1A. II. Pharmacokinetics and immune response". J. Natl. Cancer Inst. 80:937-942 (1988).

Laubser et al., "Inhibition of Complement, Neutrophil, and Platelet Activation by an Anti-Factor D Antibody During Extracorporeal Circulation", Presented at the Annual Meeting of American Society of Anesthesiologists, San Francisco, California, Oct. 14-18, 2000 (Abstract A-657).

Miller et al., "Monoclonal antibody therapeutic trials in seven patients with T-cell lymphoma". Blood, 62:988-995 (1983).

Mulligan et al., "Protective Effects of Soluble CR1 in Complement and Neutrophil-Medicated Tissue Injury", J. Immunol., 148(5):1479-1485 (1992).

Narayana et al., "Structure of Human Factor D:A Complement System Protein at 20.degree. Resolution", J. Mol. Biol., 235: 695-708 (1994).

Niemann et al., "The Use of Monoclonal Antibodies as Probes of the Three Dimensional Structure of Human Complement Factor D", J. Immunol., 132(2): 809-815 (1984).

Ray et al., "Thrombin Receptor: A Novel Target for Antiplatelet Drug Development", Thrombosis Research, 87(1): 37-50 (1997).

Riechmann et al., "Reshaping human antibodies for therapy". Nature, 332:323-327 (1988).

Sears et al., "Effects of monoclonal antibody immunotherapy on patients with gastrointestinal adenocarcinoma". J. Biol. Response Modifiers. 3:138-150 (1984).

Shawler et al., Human immune response to multiple injections of murine monoclonal IgG. J. Immunol. 135(2):1530-1535 (1985).

Sim et al., "Serine Proteases of the Complement System", Biochemical Society Transactions, vol. 28, Pt.5, pp. 545-550 (2000).

Sims et al., "A humanized CD18 antibody can block function without cell destruction". J. Immunol., 151(4):2296-2308 (1993).

Ündar et al., "Novel Anti-Factor D Monoclonal Antibody Inhibits Complement, Neutrophil, and Platelet Activation in a Simulated Pediatric Cardiopulmonary Bypass Circuit"., Presented in the $46^{th}$ Annual Conference of the American Society for Artificial Internal Organs, New York, N.Y., Jun. 28-Jul. 1, 2000, (Abstract).

Verhoeyen et al., "Reshaping human antibodies: grafting an antilysozyme activity". Science, 239:1534-1536 (1988).

Volanakis et al., "Complement Enzymes", In: *The Human Complement System in Health & Disease*, Chapter 4, pp. 49-81, Eds., J. Volonakis & M. M. Frank, Published by Marcel Dekker, Inc. New York (1998).

Volanakis et al., "Complement Factor D, A Novel Serine Protease", Protein Science, 5:553-564 (1996).

White et al., "Human Adipsin is Identical to Complement Factor D and is Expressed at High Levels in Adipose Tissue", J. Bio. Chem, 267(13): 9210-9213 (1992).

International Search Report, dated Jun. 26, 2008, of PCT/US2007/083172 now, WO 2008/055206.

International Preliminary Report on Patentability, dated May 2, 2009, of PCT/US2007/083172 now, WO 2008/055206.

Written Opinion, dated dated May 2, 2009, of PCT/US2007/083172 now, WO 2008/055206.

Amsterdam et al., "Limitation of reperfusion injury by a monoclonal antibody to C5a during myocardial infarction in pigs" *Am J Physiol*. 268(1 Pt 2):H448-57 (Jan. 1995).

Bertozzi et al., "An ELISA for selectins based on binding to a physiological ligand" *J Immunol Methods* 203(2):157-65 (Apr. 25, 1997).

Gao et al., "An enzyme-linked immunosorbent assay to identify inhibitors of activation of platelet integrin alpha IIb beta 3" *J Immunol Methods* 181(1):55-64 (Apr. 12, 1995).

Holers, "Principles and Practice" *Clinical Immunology*, R.R. Rich edition, Mosby Press pp. 363-391 (1996).

Homeister et al., "Soluble complement receptor type 1 prevents human complement-mediated damage of the rabbit isolated heart" *J Immunol*. Feb. 1, 1993;150(3):1055-64 150(3):1055-64 (Feb. 1, 1993).

Houghten et al., "The use of synthetic peptide combinatorial libraries for the identification of bioactive peptides" *Biotechniques* 13(3):412-21 (Sep. 1992).

Janeway et al., *Immunobiology* (13-5 to 13-7), 3rd edition, London, England:Current Biology Ltd, (1997).

Klohs et al., "Inhibitors of tyrosine kinase" *Curr Opin Oncol*. 19 9(6):562-8 (Nov. 1997).

Kroshus et al., "Complement inhibition with an anti-C5 monoclonal antibody prevents acute cardiac tissue injury in an ex vivo model of pig-to-human xenotransplantation" *Transplantation* 60(11):1194-202 (Dec. 15, 1995).

Lam et al., "Application of combinatorial library methods in cancer research and drug discovery" *Anticancer Drug Des*. 12(3):145-67 (Apr. 1997).

Lesavre and Eberhard, "Mechanism of action of factor D of the alternative complement pathway." *J Exp Med*. 148(6):1498-509 (Dec. 1, 1978).

Morgan, "Clinical complementology: recent progress and future trends.Morgan BP." *Eur J Clin Invest*. 24(4):219-28 (Apr. 1994).

Omer et al., "CA1A2X-competitive inhibitors of farnesyltransferase as anti-cancer agents" *Trends Pharmacol Sci*. 18(11):437-44 (Nov. 1997).

Pascual et al., "A monoclonal antibody which blocks the function of factor D of human complement" *J Immunol Methods* 127(2):263-9 (Mar. 9, 1990).

Pascual et al., "Inhibition of complement alternative pathway in mice with Fab antibody to recombinant adipsin/factor D" *Eur J Immunol*. 23(6):1389-92 (Jun. 1993).

Rabinovici et al., "Role of complement in endotoxin/platelet-activating factor-induced lung injury" *J Immunol*. 149(5):1744-50 (Sep. 1, 1992).

Ray et al., "Thrombin receptor: a novel target for antiplatelet drug development." *Thromb Res*. 87(1):37-50 (Jul. 1, 1997).

Rinder et al., "Blockade of C5a and C5b-9 generation inhibits leukocyte and platelet activation during extracorporeal circulation" *J Clin Invest.* 96(3):1564-72 (Sep. 1995).

Sahu et al., "Identification of multiple sites of interaction between heparin and the complment system" *Mol Immunol.* 30(7):679-84 (May 1993).

Sato et al., "A new method for studying the binding of human IgE to CD23 and the inhibition of this binding" *J Immunol Methods* 209(1):59-66 (Nov. 10, 1997).

Stadel et al., "Orphan G protein-coupled receptors: a neglected opportunity for pioneer drug discovery" *Trends Pharmacol Sci.* 18(11):430-7 (Nov. 1997).

Strawn et al., "Flk-1 as a target for tumor growth inhibition" *Cancer Research* 56(15):3540-5 (Aug. 1, 1996).

Tanhehco et al., "The anti-factor D antibody, MAb 166-32, inhibits the alternative pathway of the human complement system" *Transplant Proc.* 31(5):2168-71 (Aug. 1999).

Volanakis et al., "Renal filtration and catabolism of complement protein D" *N Engl J Med.* 312(7):395-9 (Feb. 14, 1985).

Wang et al., "Amelioration of lupus-like autoimmune disease in NZB/WF1 mice after treatment with a blocking monoclonal antibody specific for complement component C5" *Proc Natl Acad Sci U S A.* 93(16):8563-8 (Aug. 6, 1996).

Wang et al., "Anti-C5 monoclonal antibody therapy prevents collagen-induced arthritis and ameliorates established disease" *oc Natl Acad Sci U S A.* 92(19):8955-9 (Sep. 12, 1995).

Weisman et al., "Soluble human complement receptor type 1: in vivo inhibitor of complement suppressing post-ischemic myocardial inflammation and necrosis" *Science* 249(4965):146-51 (Jul. 13, 1990).

Wilson et al., "A competitive inhibition ELISA for the quantification of human interferon-gamma" *J Immunol Methods* 162(2):247-55 (Jun. 18, 1993).

Ambati, J. et al., 2003, "An animal model of age-related macular degeneration in senescent Ccl-2 or Ccr-2-deficient mice." Nat. Med., 9(11):1390-7 Epub Oct. 19, 2003).

Anderson, D.H., et al.. 2002, "A role for local inflammation in the formation of drusen in the aging eye." Am. J. Ophthalmol., 134:411-31.

Bok, D., 2005, "Evidence for an inflammatory process in age-related macular degeneration gains new support." Proc. Natl. Acad. Sci. (USA). 102:7053-4.

Bora, et al., 2005, "Role of Complement and Complement Membrane Attack Complex in Laser-Induced Choroidal Neovascularization." J. of Immunol. 174: 491-497.

Brown et al., 2007. "Mechanisms of disease: the complement system in renal injury—new ways of looking at an old foe." Nat Clin Pract Nephrol. 3(5):277-86.

Esparza-Gordillo, J., et al., 2004, "Genetic and environmental factors influencing the human factor H plasma levels." Immunogenetics, 56:77-82.

Farries, T.C., et al., 1990, "The mechanism of activation of the alternative pathway of complement by cell-bound C4b." Mol. Immunol., 27:1155-116.

Fung, M. et al., 2000, "Inhibition of Complement, Neutrophil, and Platelet Activation by an Anti-Factor D Antibody During Extracorporeal Circulation". Presented in the 18th Annual Houston Conference on Biomedical Engineering Research, Houston, Texas. Feb. 10-11, 2000 (Abstract).

Hageman, G.S., et al., 2001, "An integrated hypothesis that considers drusen as biomarkers of immune-mediated processes at the RPE-Bruch's membrane interface in aging and age-related macular degeneration." Prog. Retin. Eye Res., 20:705-32.

Haines, J.L., et al., 2005, "Complement factor H variant increases the risk of age-related macular degeneration." Science., 308:419-21.

Inagi et al., 1993. "Decreased Activity of Complement-Mediated Immune Complex Clearance in Hemodialysis Patients," Clin. Immune & Immunopath. 68(3):333-339.

International Search Report dated Aug. 10, 2007 of PCT/US06/043103, now WO 2007/056227.

Janeway et al., 1997, *Immunobiology* 3<sup>rd</sup> Edition, Cuurent Biology Ltd, London England 13: 5-8.

Johnson, L.V., et al., 2001, "Complement activation and inflammatory processes in Drusen formation and age related macular degeneration." Exp. Eye Res., 73:887-96.

Krzystolik M. G., et al., 2002, "Prevention of experimental choroidal neovascularization with intravitreal anti-vascular endothelial growth factor antibody fragment." Arch Ophthalm., 120:338-346.

Matson et al., 2000, "Evolving concepts of therapy for sepsis and septic shock and the use of hyperpermeable memberanes", Current Opinion in Critical Care 6:431-436.

Notice of Allowance dated Jan. 6, 2011 for U.S. Appl. No. 11/478,088. filed Jun. 29, 2006.

Ricklin and Lambris, 2007, "Complement-targeted therapeutics." Nat Biotechnol. 25(11):1265-75.

Rodriguez De Cordoba S., et al., 2004, "The human complement factor H: functional roles, genetic variations and disease associations." Mol. Immunol. 41:355-67.

Written Opinion dated Aug. 10, 2007 of PCT/US06/043103, now WO 2007/056227.

Zareparsi, S., et al., 2005, "Strong association of the Y402H variant in complement factor H at 1q32 with susceptibility to age-related macular degeneration." Am J Hum Genet. 77:149-53.

International Search Report dated Sep. 15, 2009 of PCT/US09/41785, now WO 2009/134711.

Written Opinion dated Oct. 28, 2010 of PCT/US09/41785, now WO 2009/134711.

U.S. Appl. No. 09/253,689, filed Feb. 20, 1999, Fung et al.

U.S. Appl. No. 13/081,203, filed Apr. 6, 2011, Fung et al.

Accession NM_001928 "Homo sapiens complement factor D (adipsin) (cFD), mRNA" dated Mar. 12, 2011.

Aderem et al., 1999, "Mechanisms of phagocytosis in macrophages." Annu. Rev. Immunol. 17: 593-623.

Akif et al., 2002, "Novel anti-factor D monoclonal antibody inhibits complement and leukocyte activation in baboon model of cardiopulmonary bypass." Annals of Thoracic Surgery 74(2):355-362.

Amit et al., 1986 "Three dimensional Structure of an Antigen-Antibody Complex at 2.8A Resolution." Science 233:747-753.

Arrate et al., 2001."Cloning of human junctional adhesion molecule 3 (JAM3) and its identification as the JAM2 counter-receptor." J Biol. Chem.. 276(49):45826-45832.

Attwood, 2000. "The Babel of bioinformatics." Science 290:471-473.

Barnum et al., 1984, "Quantification of complement factor D in human serum by a solid phase radioimmunoassay." Immunol Methods 67(2):303-9.

Blast Report, http://expasy.org/cgi-bininiceprot.pl/printable?ac=Q80WA3, dated Mar. 1, 2004.

Bora et al., 2006, "Complement activation via alternative pathway is critical in the development of laser-induced choroidal neovascularization: role of factor B and factor H." J Immunol. 177:1872-8.

Brown. 1992, "Complement receptors, adhesion, and phagocytosis," Infectious agents and disease, I :63-70.

Carroll. 2004, "The complement system in regulation of adaptive immunity." Nat. Immunol. 5(10):981-986.

Casset et al., 2003, "A peptide mimetic of an anti-CD4 monoclonal antibody by rational design." Biochem Biophys Res Comm. 307:198-205.

Chample et al., 1995, "Monoclonal antibodies that block the activity of leukocyte function-associated antigen I recognize three discrete epitopes in the inserted domain of CD11a"J Biol. Chem. 270:1388-1394.

Chen et al, 1999. "Selection and analysis of an optimized anti-VEGF antibody: crystal structure of an affinity-matured Fab in complex with antigen." J Mol. Biol. 293:865-881.

Database Genbank (Apr. 24, 2001), "Human Pro 1868 Protein" Database Accession No. AAB80272 XP002448361, dated Jun. 15. 2007.

Edwards et al., 2005, "Complement factor H polymorphism and age-related macular degeneration," Science 308: 419-421.

Ferris et al., 2005, "A simplified seveity scale for age-related macular degeneration," Arch Opthalmol. 123:1570-74.

Hageman et al., 2005, "A common haplotype in the complement regulatory gene factor H (HFI/CFH) predisposes individuals to age-related macular degeneration." Proc. Natl. Acad Sci. 102(20): 7227-7232.

Harlow et al., 1988. "Chapter 14: Immunoassays." Antibodies, A Laboratory Manula. Cold spring harbor pp. 553-612.

Holers et al., 1992, "The evolution of mouse and human complement C3-binding proteins: divergence of form but conversation of function." Immnol. Today I3(6):231-236.

Holm et al., 2007, "Functional mapping and single chain construction of the anti-cytokeratin 8 monoclonal antibody TS1."44(6):1075-1084.

Jaffe et al., 2006 Intraocular Drug Delivery. Taylor and Francis pp. 85-95,111-128, 193-202, 203-255, 249-263.

Jager et al., 2008, "Age-related macular degeneration." New Engl J med. 359(16): 1735-6.

Janssen et al., 2007. "Structural insights into the central complement component C3." Molec. Immunol. 44:3-10.

Katschke et al., 2007, "A Novel inhibitor of the alternative pathway of complement reverses inflammation and bone destruction in experimental arthritis." Brief Definitive Report 204(6): 1319-1325.

Kim et al.. 2005, "Characterization of monoclonal antibody specific to the Z3291g protein, a member of immunoglobulin superfamily." Immunol. Letters 99:153-161.

Klein et al., 2005. "Complement Factor H Variant Increases the Risk of Age-Related Macular Degeneration," Science, 308:385-389.

Kostavasilli et al., 1997, "Mechanism of complement inactivation by glycoprotein c of herpes simplex virus." Immunol. 158(4): 1763-71.

Langnaese et al., 2000. "Cloning of Z391g, a novel gene with immunoglobulin-like domains located on human chromosome XI" BBA, 552-555.

Lee et al., 2006, "Z391g is expressed on macrophages and may mediate inflammatory reactions in arthritis and artherosclerosis." J of Leukocyte boil. 80: 922-928.

MacCallum et al., 1996, "Antibody-antigen interactions: contact analysis and binding site topography" J Mol Bol 262:732-745.

Makrides et al., 1998, "Therapeutic Inhibition of the Complement System." Pharmacological Reviews. 50(1 ):59-87.

Morley & Walport, 2000, "Factor D" Complements Facts Book, 17, 69-72.

Padlan et al, 1989, "Structure of an antibody-antigen complex: crystal structure of the HyHEL-10 Fab-lysozyme complex." Proc. Natl. Acad Sci 1989:5938-5942.

Paul. 1993, Fundamental Immunology, 3$^{rd}$ edition, raven press. 292-295.

Petrukhin et al., 2007, "New therapeutic targets in atrophic age-relaed macular degeneration." Expert Opinion on Therapeutic targets 11(5):625-639.

Powell et al., 1996. "A compendium and hydropathy/flexibility analysis of common reactive sites in proteins: reactivity at Asn, Asp, Gln, and Met motifs in neutral pH solution" Pharm Biotech 9:1-140.

Pyz et al., 2006. "C-type lectin-like receptors on myeloid cells." Annals of Med 38:242-251.

Rohrer et al., 2009. "A targeted inhibitor of the alternative complement pathway reduces angiogenesis in a mouse model of age-related macular degeneration." Invest Ophthalmol Vis Sci. (7):3056-64.

Ross et al., 1985. "Membrane complement receptors specific for bound fragments of C3." Advances in Immunol. 37:217-267.

Rudikoff et al., 1982, "Single amino acid substitution altering antigen-binding specificity." Proc. Natl. Acad Sci 79(6):1979-1983.

Sallo et al., 2009. "The International Classification system and the progression of age-related macular degeneration." Curr Eye. Res. 34(3):238-40.

Skolnick et al., 2000, "From genes to protein structure and function: novel applications of computational approaches in the genomic era." Trends in Biotech 18: 34-39.

Strausberg et al., 2002, "Generation and initial analysis of more than 15,000 full-length human and mouse cDNA se uences," Proc. Natl. Acad Sci. 99:26 —16899-16903.

Stuart et al., 2005, "Phagocytosis: Elegant complexity." Immunity 22:539-550.

Taylor et al., 2005, "Macrophage receptors and immune recognition", Annu. Rev. ImmunoL, 23: 901-944.

Taylor et al., 2003, "Pattern recognition receptors and differentiation antigens define murine myeloid cell heterogeneity ex vivo." Eur. J. Immunol. 33:2090-2097.

Thurman et al., 2006, "The central role of the alternative complement pathway in human disease." J immunol. 176:1305-1310.

Tsukita et al., 2001. "Multifunctional strands in tight junctions." Nat. Revew. 2:285-293.

Underhill eta I., 2002, "Phagocytosis of microbes: Complexity in action." Annu Rev. Immunol. 20:825-852.

Vajdos et al., 2002, "Comprehensive functional maps of the antigen-binding site of an anti-ErbB2 antibody obtained with shotgun scanning mutagenesis." J. Mol. Biol. 320(2):415-428.

Walker et al., 2002, "Z391g is co-expressed with activation macrophage genes." Biochemica et Biophysica Acta 1574:387-390.

Walport, 2001 "Complement first of two parts." Advances in Immunol. Neng J med 344(14): 1058-1066.

Weisman et al., 2006, "Structure of C3b in complex with CRIg gives insignt into regulation of complement activation." Nature 444(71 16):217-20.

Wu et al., 1999. "Humanization of a murine monoclonal antibody by simultaneous optimization of framework and CRD residues." JMB 294:151-162.

Pascual et al., 1988, Metabolism of complement factor D in renal failure. Kidney International 34(4):529-36.

Written Opinion dated Nov. 24, 2009 of PCT/US2008/064526, now WO 2008/147883.

International Preliminary Examination Report, dated Nov. 24, 2009 of PCT/US2008/064526. now WO 2008/147883.

International Search Report, dated Aug. 14, 2008, of PCT/US2008/064526, now WO 2008/147883.

U.S. Appl. No. 13/007,061, filed Jan. 14, 2011, An et al.

Zeng et al.. 2010, "Lack of Association of CFDpolymorphisms with advanced age-related macular degeneration." Molec. Vis. 16:2273-2278.

FIGURE 1A

Amino Acid Sequence of the Variable Heavy Chain of Murine MAb 166-32

QIQLVQSGPELKKPGETVKISCKASGYTFTNYGMNWVKQAPGKGLKWMGWINT
YTGETTYADDFKGRFVFSLETSASTAYLEINNLKNEDMATYFCEREGGVDNWG
QGTTLTVSS (SEQ ID NO: 1)

FIGURE 1B

Amino Acid Sequence of the Variable Light Chain of Murine MAb 166-32

ETTVTQSPASLSMAIGEKVTIRCITSTDIDDDMNWYQQKPGEPPKLLISGGNTLR
PGVPSRFSSSGYGADFVFTIDNMLSEDVADYYCLQSDNLPYTFGGGTRLEIK
(SEQ ID NO: 2)

FIGURE 2A

Murine Nucleic Acid Sequence for Heavy Chain Variable Region of MAb 166-32

CAGATCCAGTTGGTGCAGTCTGGACCTGAGCTGAAGAAGCCTGGAGAGACA
GTCAAGATCTCCTGCAAGGCTTCTGGGTATACCTTCACAAACTATGGAATGA
ACTGGGTGAAGCAGGCTCCAGGAAAGGGTTTAAAGTGGATGGGCTGGATAA
ACACCTACACTGGAGAGACAACATATGCTGATGACTTCAAGGGACGGTTTGT
CTTCTCTTTGGAAACCTCTGCCAGCACTGCCTATTTGGAGATCAACAACCTCA
AAAATGAGGACATGGCTACATATTTCTGTGAAAGAGGGGGGGGTTGACAA
CTGGGGCCAAGGCACCACTCTCACAGTCTCCTCA (SEQ ID NO: 3)

FIGURE 2B

Murine Nucleic Acid Sequence for Light Chain Variable Region of MAb 166-32

GAAACAACTGTGACCCAGTCTCCTGCATCCCTGTCCATGGCTATAGGAGAAAA
AGTCACCATCAGATGCATAACCAGCACTGATATTGATGATGATATGAACTGGT
ACCAGCAGAAGCCAGGGGAACCTCCTAAGCTCCTTATTTCAGGAGGCAATACT
CTTCGTCCTGGAGTCCCATCCCGATTCTCCAGCAGTGGCTATGGTGCAGATTTT
GTTTTTACAATTGACAACATGCTCTCAGAAGATGTTGCAGATTACTACTGTTTG
CAAAGTGATAACTTGCCGTACACGTTCGGAGGGGGGACCAGGCTGGAAATAA
AA (SEQ ID NO: 4)

FIGURE 3 Comparison of Human Heavy Chain Template to Murine MAb 166-32

```
              1              10                  20                  30                40
Mu 166-32     Q I Q L V Q S G P E L K K P G E T V K I S C K A S G Y T F T N Y G M N W V K Q A P G K G L K W M G
Hu VI-4.1b+                   V       S                       G Y T F T S Y A M N       K       Q         E 50 52 a 53                60              65              70      80 82 a b c 83              90
Mu 166-32     W I N T Y T G E T T Y A D D D F K G R F V F S L E T S A S T A Y L E I N N L K N E D M A T Y F C E R
Hu VI-4.1b+   W I N T N T G N P T Y A Q G F T G   D V             Q     S S         A     T   V         A 95              103         110 113
Mu. 166-32    E G G V D N W G Q G T T L T V S S
Hu VI-4.1b+       Y F D Y             L V      (JH4d)
```

Kabat CDR: underlined.   Bold/Italic: Chothia CDR1.

FIGURE 4

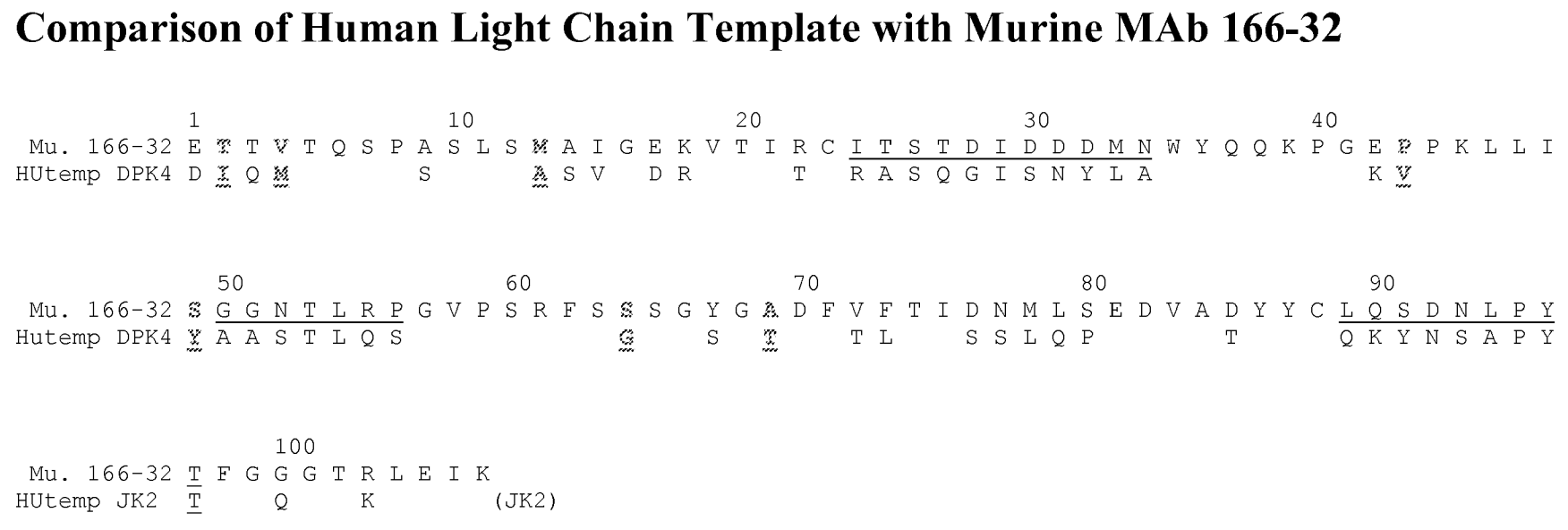

Comparison of Human Light Chain Template with Murine MAb 166-32

```
              1                   10                  20                  30                  40
Mu. 166-32    E  T  T  V  T  Q  S  P  A  S  L  S  M  A  I  G  E  K  V  T  I  R  C  I  T  S  T  D  I  D  D  D  M  N  W  Y  Q  Q  K  P  G  E  P  P  K  L  L  I
HUtemp DPK4   D  I  Q  M              S              A  S  V           D  R        T        R  A  S  Q  G  I  S  N  Y  L  A                       K  V 50                  60                  70                  80                  90
Mu. 166-32    S  G  G  N  T  L  R  P  G  V  P  S  R  F  S  S  S  G  Y  G  A  D  F  V  F  T  I  D  N  M  L  S  E  D  V  A  D  Y  Y  C  L  Q  S  D  N  L  P  Y
Hutemp DPK4      A  A  S  T  L  Q  S                             G     S  T           T  L        S  S  L  Q  P              T     Q  K  Y  N  S  A  P  Y 100
Mu. 166-32    T  F  G  G  G  T  R  L  E  I  K        (JK2)
HUtemp JK2    T  T           Q           K
```

FIGURE 5

#56 VK
DIQVTQSPSSLSASVRDRVTITC<u>itstdidddmn</u>WYQQKPGKVPKLLIS<u>ggntlrp</u>GVPSRFSGSGSGTD
FTLTISSLQPEDVATYYC<u>lqsdnlpyt</u>FGQGTKLEIK

#56 VH
QVQLVQSGPELKKPGASVKVSCKAS<u>gytftnygmn</u>WVKQAPGQGLE<u>wmgwintytgettyaddfk</u>GRFVF
SLDTSVSTAYLQISSLKAEDTATYYCER<u>eggvdn</u>WGQGTLVTVSS

#111 VK
DIQVTQSPSSLSASVGDRVTITC<u>itstdidddmn</u>WYQQKPGKVPKLLIS<u>ggntlrp</u>GVPSRFSGSGSGTD
FTLTISSLQPEDVATYYC<u>lqsdslpyt</u>FGQGTKLEIK

#111 VH
QVQLVQSGPELKKPGASVKVSCKAS<u>gytftnygmn</u>WVRQAPGQGLE<u>wmgwintytgettyaddfk</u>GRFVF
SLDTSVSTAYLQISSLKAEDTAVYYCER<u>eggvnn</u>WGQGTLVTVSS

#250 VK
DIQVTQSPSSLSASVGDRVTITC<u>itstdidddmn</u>WYQQKPGKVPKLLIS<u>hgntlrp</u>GVPSRFSGSGSGTD
FTLTISSLQPEDVATYYC<u>lqsdslpyt</u>FGQGTKLEIK

#250 VH
QVQLVQSGPELKKPGASVKVSCKAS<u>gytftnygln</u>WVRQAPGQGLE<u>wmgwintytgettyaddfk</u>GRFVFS
LDTSVSTAYLQISSLKAEDTAVYYCER<u>eggvnn</u>WGQGTLVTVSS

#416 VK
DIQVTQSPSSLSASVGDRVTITC<u>itstdidddmn</u>WYQQKPGKVPKLLIS<u>dgntlrp</u>GVPSRFSGSGSGTD
FTLTISSLQPEDVATYYC<u>lqsdslpyt</u>FGQGTKLEIK

#416 VH
QVQLVQSGPELKKPGASVKVSCKAS<u>gytftsygmn</u>WVRQAPGQGLE<u>wmgwintytgettyaddfk</u>GRFVF
SLDTSVSTAYLQISSLKAEDTAVYYCER<u>eggvnn</u>WGQGTLVTVSS Inhibition Of The Alternative Complement Activity Of Human Serum By Different TNX-238 Humanized Fab Constructs In Hemolytic Assay

| | | | | | | | | | | | | | | | | | | | | | | | |
|---|---|---|---|---|---|---|---|---|---|---|---|---|---|---|---|---|---|---|---|---|---|---|---|
| A | Q V Q L V Q S G A E V K K P G A S V K V S C K A S | G Y T F T | -H1- | W V R Q A P G Q G L E W M G | -H2- |
| B | Q V Q L V Q S G A E V K K P G A S V K V S C K A S | | -H1- | W V R Q A P G Q G L E W M | -H2- |
| C | Q V Q L V Q S G A E V K K P G A S V K V S C K A S | | -H1- | W V R Q A P G Q G L E W M | -H2- |
| D | Q V Q L V Q S G A E V K K P G A S V K V S C K A S | | -H1- | W V R Q A P G Q G L E W M | -H2- |

II

| | | | | | |
|---|---|---|---|---|---|
| A | Q V Q L Q E S G P G L V K P S Q T L S L T C T V S | G G S V S | -H1- | W I R Q P P G K G L E W I G | -H2- |
| B | Q V Q L Q E S G P G L V K P S Q T L S L T C T V S | | -H1- | W I R Q P P G K G L E W I | -H2- |
| C | Q V Q L Q E S G P G L V K P S Q T L S L T C T V S | | -H1- | W I R Q P P G K G L E W I | -H2- |
| D | Q V Q L Q E S G P G L V K P S Q T L S L T C T V S | | -H1- | W I R Q P P G K G L E W I | -H2- |

III

| | | | | | |
|---|---|---|---|---|---|
| A | E V Q L V E S G G G L V Q P G G S L R L S C A A S | G F T F S | -H1- | W V R Q A P G K G L E W V S | -H2- |
| B | E V Q L V E S G G G L V Q P G G S L R L S C A A S | | -H1- | W V R Q A P G K G L E W V | -H2- |
| C | E V Q L V E S G G G L V Q P G G S L R L S C A A S | | -H1- | W V R Q A P G K G L E W V | -H2- |
| D | E V Q L V E S G G G L V Q P G G S L R L S C A A S | | -H1- | W V R Q A P G K G L E W V | -H2- |

VII

| | | | | | |
|---|---|---|---|---|---|
| A | Q V Q L V Q S G S E L K K P G A S V K V S C K A S | G Y T F T | -H1- | W V R Q A P G Q G L E W M G | -H2- |
| B | Q V Q L V Q S G S E L K K P G A S V K V S C K A S | | -H1- | W V R Q A P G Q G L E W M | -H2- |
| C | Q V Q L V Q S G S E L K K P G A S V K V S C K A S | | -H1- | W V R Q A P G Q G L E W M | -H2- |
| D | Q V Q L V Q S G S E L K K P G A S V K V S C K A S | | -H1- | W V R Q A P G Q G L E W M | -H2- |

Acceptor

| | | | | | |
|---|---|---|---|---|---|
| A | E V Q L V E S G G G L V Q P G G S L R L S C A A S | G F N I K | -H1- | W V R Q A P G K G L E W V S | -H2- |
| B | E V Q L V E S G G G L V Q P G G S L R L S C A A S | | -H1- | W V R Q A P G K G L E W V | -H2- |
| C | E V Q L V E S G G G L V Q P G G S L R L S C A A S | | -H1- | W V R Q A P G K G L E W V | -H2- |
| D | E V Q L V E S G G G L V Q P G G S L R L S C A A S | | -H1- | W V R Q A P G K G L E W V | -H2- |

Second Acceptor

| | | | | | |
|---|---|---|---|---|---|
| A | E V Q L V E S G G G L V Q P G G S L R L S C A A S | G F N I K | -H1- | W V R Q A P G K G L E W V S | -H2- |
| B | E V Q L V E S G G G L V Q P G G S L R L S C A A S | | -H1- | W V R Q A P G K G L E W V | -H2- |
| C | E V Q L V E S G G G L V Q P G G S L R L S C A A S | | -H1- | W V R Q A P G K G L E W V | -H2- |
| D | E V Q L V E S G G G L V Q P G G S L R L S C A A S | | -H1- | W V R Q A P G K G L E W V | -H2- |

FIGURE 8B

| | | | | |
|---|---|---|---|---|
| R V T I T A D T S T S T A Y M E L S S L R S E D T A V Y Y C A R | -H3- | W G Q G T L V T V S S | SEQ ID NO: 28 |
| R V T I T A D T S T S T A Y M E L S S L R S E D T A V Y Y C A R | -H3- | W G Q G T L V T V S S | SEQ ID NO: 29 |
| R V T I T A D T S T S T A Y M E L S S L R S E D T A V Y Y C A R | -H3- | W G Q G T L V T V S S | SEQ ID NO: 30 |
| R V T I T A D T S T S T A Y M E L S S L R S E D T A V Y Y C | -H3- | W G Q G T L V T V S S | SEQ ID NO: 31 |
| R V T I S V D T S K N Q F S L K L S S V T A A D T A V Y Y C A R | -H3- | W G Q G T L V T V S S | SEQ ID NO: 32 |
| R V T I S V D T S K N Q F S L K L S S V T A A D T A V Y Y C A R | -H3- | W G Q G T L V T V S S | SEQ ID NO: 33 |
| R V T I S V D T S K N Q F S L K L S S V T A A D T A V Y Y C A | -H3- | W G Q G T L V T V S S | SEQ ID NO: 34 |
| R V T I S V D T S K N Q F S L K L S S V T A A D T A V Y Y C | -H3- | W G Q G T L V T V S S | SEQ ID NO: 35 |
| R F T I S R D N S K N T L Y L Q M N S L R A E D T A V Y Y C A R | -H3- | W G Q G T L V T V S S | SEQ ID NO: 36 |
| R F T I S R D N S K N T L Y L Q M N S L R A E D T A V Y Y C A R | -H3- | W G Q G T L V T V S S | SEQ ID NO: 37 |
| R F T I S R D N S K N T L Y L Q M N S L R A E D T A V Y Y C A | -H3- | W G Q G T L V T V S S | SEQ ID NO: 38 |
| R F T I S R D N S K N T L Y L Q M N S L R A E D T A V Y Y C | -H3- | W G Q G T L V T V S S | SEQ ID NO: 39 |
| R F V F S L D T S V S T A Y L Q I S S L K A E D T A V Y Y C A R | -H3- | W G Q G T S L T V S S | SEQ ID NO: 55 |
| R F V F S L D T S V S T A Y L Q I S S L K A E D T A V Y Y C A R | -H3- | W G Q G T S L T V S S | SEQ ID NO: 56 |
| R F V F S L D T S V S T A Y L Q I S S L K A E D T A V Y Y C A | -H3- | W G Q G T S L T V S S | SEQ ID NO: 57 |
| R F V F S L D T S V S T A Y L Q I S S L K A E D T A V Y Y C | -H3- | W G Q G T S L T V S S | SEQ ID NO: 58 |
| R F T I S A D T S K N T A Y L Q M N S L R A E D T A V Y Y C S R | -H3- | W G Q G T L V T V S S | SEQ ID NO: 40 |
| R F T I S A D T S K N T A Y L Q M N S L R A E D T A V Y Y C S R | -H3- | W G Q G T L V T V S S | SEQ ID NO: 41 |
| R F T I S A D T S K N T A Y L Q M N S L R A E D T A V Y Y C S | -H3- | W G Q G T L V T V S S | SEQ ID NO: 42 |
| R F T I S A D T S K N T A Y L Q M N S L R A E D T A V Y Y C A R | -H3- | W G Q G T L V T V S S | SEQ ID NO: 43 |
| R F T I S A D T S K N T A Y L Q M N S L R A E D T A V Y Y C A R | -H3- | W G Q G T L V T V S S | SEQ ID NO: 44 |
| R F T I S A D T S K N T A Y L Q M N S L R A E D T A V Y Y C A | -H3- | W G Q G T L V T V S S | SEQ ID NO: 45 |
| R F T I S A D T S K N T A Y L Q M N S L R A E D T A V Y Y C | -H3- | W G Q G T L V T V S S | SEQ ID NO: 46 |

FIGURE 9A

κv1  DIQMTQSPSSLSASVGDRVTITC-[L1]-WYQQKPGKAPKLLIY-[L2]-GVPSRFSGSGSGTDFTLTISSLQP

κv2  DIVMTQSPLSLPVTPGEPASISC-[L1]-WYLQKPGQSPQLLIY-[L2]-GVPDRFSGSGSGTDFTLKISRVEA

κv3  EIVLTQSPGTLSLSPGERATLSC-[L1]-WYQQKPGQAPRLLIY-[L2]-GIPDRFSGSGSGTDFTLTISRLEP

κv4  DIVMTQSPDSLAVSLGERATINC-[L1]-WYQQKPGQPPKLLIY-[L2]-GVPDRFSGSGSGTDFTLTISSLQA

FIGURE 9B

E D F A T Y Y C -L3- F G Q G T K V E I K  SEQ ID NO: 47

E D V G V Y Y C -L3- F G Q G T K V E I K  SEQ ID NO: 48

E D F A V Y Y C -L3- F G Q G T K V E I K  SEQ ID NO: 49

E D V A V Y Y C -L3- F G Q G T K V E I K  SEQ ID NO: 50

HUMANIZED ANTI-FACTOR D ANTIBODIES

This application claims benefit, under 35 U.S.C. §119(e), of U.S. Provisional Application No. 60/856,505, filed Nov. 2, 2006, which is incorporated by reference herein in its entirety.

BACKGROUND OF THE INVENTION

The complement system plays a central role in the clearance of immune complexes and the immune response to infectious agents, foreign antigens, virus-infected cells and tumor cells. However, complement is also involved in pathological inflammation and in autoimmune diseases. Therefore, inhibition of excessive or uncontrolled activation of the complement cascade could provide clinical benefit to patients with such diseases and conditions.

The complement system encompasses two distinct activation pathways, designated the classical and the alternative pathways (V. M. Holers, In *Clinical Immunology Principles and Practice*, ed. R. R. Rich, Mosby Press; 1996, 363-391). The classical pathway is a calcium/magnesium-dependent cascade which is normally activated by the formation of antigen-antibody complexes. The alternative pathway is a magnesium-dependent cascade which is activated by deposition and activation of C3 on certain susceptible surfaces (e.g. cell wall polysaccharides of yeast and bacteria, and certain biopolymer materials). Activation of the complement pathway generates biologically active fragments of complement proteins, e.g. C3a, C4a and C5a anaphylatoxins and C5b-9 membrane attack complexes (MAC), which mediate inflammatory activities involving leukocyte chemotaxis, activation of macrophages, neutrophils, platelets, mast cells and endothelial cells, vascular permeability, cytolysis, and tissue injury.

Factor D is a highly specific serine protease essential for activation of the alternative complement pathway. It cleaves factor B bound to C3b, generating the C3b/Bb enzyme which is the active component of the alternative pathway C3/C5 convertases. Factor D may be a suitable target for inhibition, since its plasma concentration in humans is very low (1.8 µg/ml), and it has been shown to be the limiting enzyme for activation of the alternative complement pathway (P. H. Lesavre and H. J. Müller-Eberhard. *J. Exp. Med.*, 1978; 148: 1498-1510; J. E. Volanakis et al., *New Eng. J. Med.*, 1985; 312: 395-401).

The down-regulation of complement activation has been demonstrated to be effective in treating several disease indications in animal models and in ex vivo studies, e.g. systemic lupus erythematosus and glomerulonephritis (Y. Wang et al., *Proc. Natl. Acad. Sci.*; 1996, 93: 8563-8568), rheumatoid arthritis (Y. Wang et al., *Proc. Natl. Acad. Sci.*, 1995; 92: 8955-8959), cardiopulmonary bypass and hemodialysis (C. S. Rinder, *J. Clin. Invest.*, 1995; 96: 1564-1572), hypercute rejection in organ transplantation (T. J. Kroshus et al., *Transplantation*, 1995; 60: 1194-1202), myocardial infarction (J. W. Homeister et al., *J. Immunol.*, 1993; 150:1055-1064; H. F. Weisman et al., *Science*, 1990; 249: 146-151), reperfusion injury (E. A. Amsterdam et al., *Am. J. Physiol.*, 1995; 268: H448-H457), and adult respiratory distress syndrome (R. Rabinovici et al., *J. Immunol.*, 1992; 149: 1744-1750). In addition, other inflammatory conditions and autoimmune/immune complex diseases are also closely associated with complement activation (V. M. Holers, ibid., B. P. Morgan. *Eur. J. Clin. Invest.*, 1994:24:219-228), including thermal injury, severe asthma, anaphylactic shock, bowel inflammation, urticaria, angioedema, vasculitis, multiple sclerosis, myasthenia gravis, membranoproliferative glomerulonephritis, and Sjögren's syndrome.

There is a need for antibody therapeutics in the field of complement-mediated disorders and the humanized antibodies of the present invention provide high affinity antibodies useful to meet this need.

SUMMARY OF THE INVENTION

The present invention relates generally to antibodies comprising the heavy and light chain variable domain sequences of murine antibody 166-32, which is an antibody capable of inhibiting biological activities associated with Factor D. For example, at a concentration of 18 µg/ml (equivalent to about 1.5 times the molar concentration of human factor D in the blood; molar ratio of anti-Factor D antibody to Factor D of about 1.5:1), significant inhibition of the alternative complement activity by the antibody can be observed (see, e.g., U.S. Pat. No. 6,956,107)

The present invention also relates to humanized antibodies of murine MAb 166-32. The invention includes the amino acid sequences of the variable heavy and light chain of the antibodies and their corresponding nucleic acid sequences. Another embodiment of the invention includes the CDR sequences of these antibodies.

Another embodiment of the present invention includes compositions comprising an antibody of the invention. In another embodiment, the invention provides cell lines and vectors harboring the antibody sequences of the present invention. In one aspect, the invention includes method of making and using antibodies and compositions of the invention.

Another embodiment of the preset invention is the use of these humanized antibodies for the preparation of a medicament or composition for the treatment of disorders associated with excessive or uncontrolled complement activation. They include complement activation during cardiopulmonary bypass operations; complement activation due to ischemia-reperfusion following acute myocardial infarction, aneurysm, stroke, hemorrhagic shock, crush injury, multiple organ failure, hypobolemic shock, intestinal ischemia or other events causing ischemia. Complement activation has also been shown to be associated with inflammatory conditions such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. It also includes autoimmune disease such as systemic lupus erythematosus, myasthenia gravis, rheumatoid arthritis, Alzheimer's disease and multiple sclerosis. Complement activation is also associated with transplant rejection. Complement activation is also associated with ocular diseases such as age-related macular degeneration, diabetic retinopathy.

BRIEF DESCRIPTION OF THE FIGURES

FIGS. 1A and 1B depict the amino acid sequence of the Murine MAb 166-32 Variable Heavy Chain (SEQ ID NO:1) (FIG. 1A) and the Variable Light Chain (SEQ ID NO:2) (FIG. 1B).

FIGS. 2A and 2B depict nucleic acid sequence of the Murine MAb 166-32 Variable Heavy Chain (SEQ ID NO:3) (FIG. 2A) and the Variable Light Chain (SEQ ID NO:4) (FIG. 2B).

FIG. 3 depicts the comparison of the heavy chain of the murine MAb 166-32 (SEQ ID NO:1).

FIG. 4 depicts the comparison of the light chain of the murine MAb 166-32 (SEQ ID NO:2).

FIG. 5 depicts the amino acid sequences of the Variable Heavy Chain and the Variable Light Chain for each humanized antibody clone #56 (SEQ ID NOs: 6 and 5), #111 (SEQ ID NOs: 8 and 7), #250 (SEQ ID NOs: 10 and 9), and #416 (SEQ ID NOs: 12 and 11).

FIG. 8A-B (variable heavy (VH) consensus frameworks) and FIG. 9A-B (variable light (VL) consensus frameworks) depict exemplary acceptor human consensus framework sequences that can be used in practicing the instant invention with sequence identifiers as follows: (FIG. 8A-B) human VH subgroup I consensus framework minus Kabat CDRs (SEQ ID NO: 28), human VH subgroup I consensus framework minus extended hypervariable regions (SEQ ID NOs: 29-31), human VH subgroup II consensus framework minus Kabat CDRs (SEQ ID NO: 32), human VH subgroup II consensus framework minus extended hypervariable regions (SEQ ID NOs: 33-35), human VH subgroup III consensus framework minus Kabat CDRs (SEQ ID NO: 36), human VH subgroup III consensus framework minus extended hypervariable regions (SEQ ID NOs: 37-39), human VH subgroup VII consensus framework minus Kabat CDRs (SEQ ID NO: 55), human VH subgroup VII consensus framework minus extended hypervariable regions (SEQ ID NOs: 56-58), human VH acceptor framework minus Kabat CDRs (SEQ ID NO: 40), human VH acceptor framework minus extended hypervariable regions (SEQ ID NOs: 41-42), human VH acceptor 2 framework minus Kabat CDRs (SEQ ID NO: 43) and human VH acceptor 2 framework minus extended hypervariable regions (SEQ ID NOs: 44-46) and (FIG. 9A-B) human VL kappa subgroup I consensus framework (SEQ ID NO: 47), human VL kappa subgroup II consensus framework (SEQ ID NO: 48), human kappa subgroup III consensus framework (SEQ ID NO: 49) and human kappa subgroup IV consensus framework (SEQ ID NO: 50).

DETAILED DESCRIPTION OF THE INVENTION

Definitions

Figure 6:
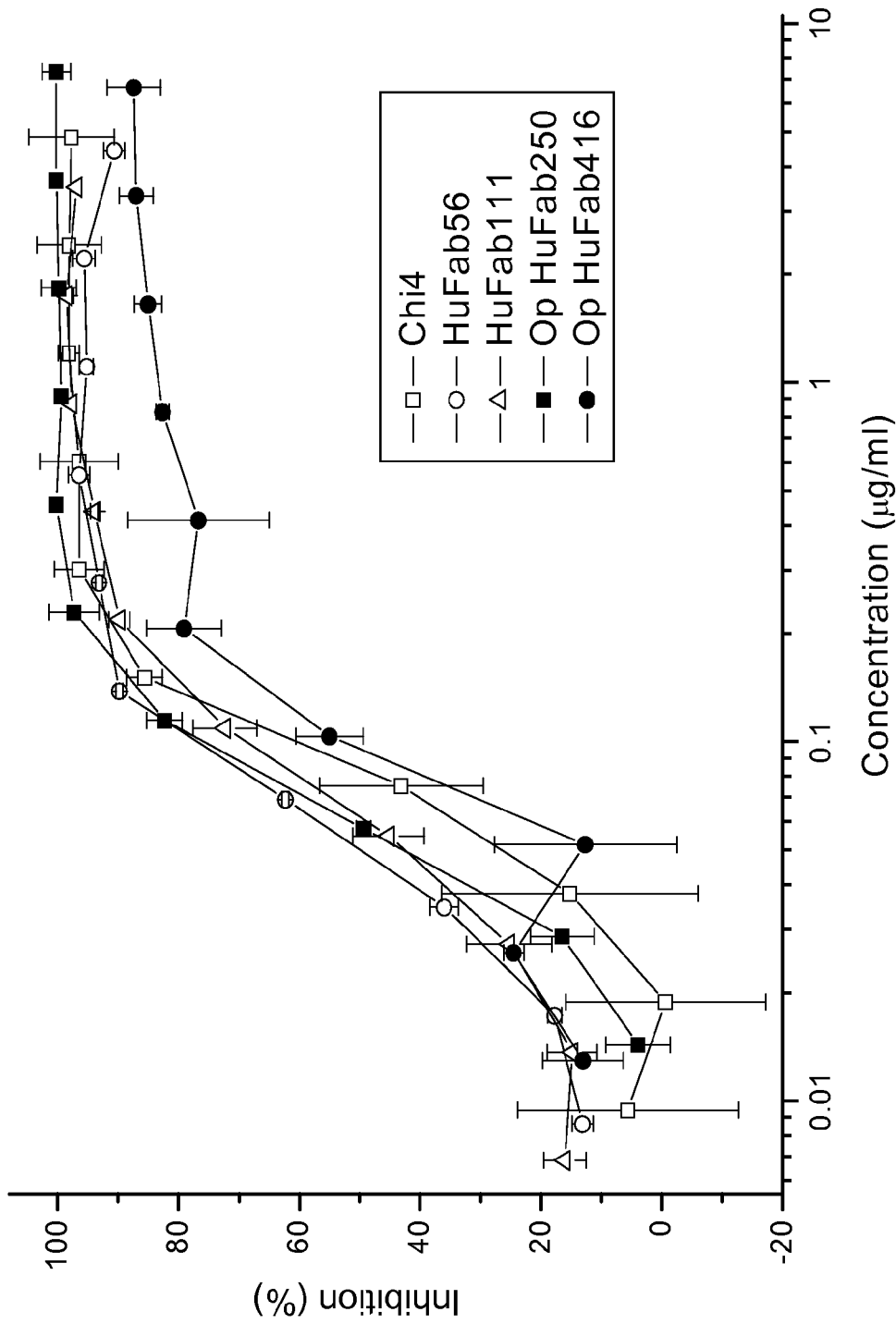
FIG. 6 depicts the hemolytic assay results for humanized antibody Fab clone #56, #111, #250, and #416.

Terms used throughout this application are to be construed with ordinary and typical meaning to those of ordinary skill in the art. However, Applicants desire that the following terms be given the particular definition as defined below.

The phrase "substantially identical" with respect to an antibody chain polypeptide sequence may be construed as an antibody chain exhibiting at least 70%, or 80%, or 90% or 95% sequence identity to the reference polypeptide sequence. The term with respect to a nucleic acid sequence may be construed as a sequence of nucleotides exhibiting at least about 85%, or 90%, or 95% or 97% sequence identity to the reference nucleic acid sequence.

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software.

The term "antibody" is used in the broadest sense, and specifically covers monoclonal antibodies (including full length monoclonal antibodies), polyclonal antibodies, and multispecific antibodies (e.g., bispecific antibodies). Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end.

As used herein, "anti-human Factor D antibody" means an antibody which specifically binds to human Factor D in such a manner so as to inhibit or substantially reduce complement activation.

The term "variable" in the context of variable domain of antibodies, refers to the fact that certain portions of the variable domains differ extensively in sequence among antibodies and are used in the binding and specificity of each particular antibody for its particular target. However, the variability is not evenly distributed through the variable domains of antibodies. It is concentrated in three segments called complementarity determining regions (CDRs) also known as hypervariable regions (HVRs) both in the light chain and the heavy chain variable domains. The more highly conserved portions of variable domains are called the framework (FR). The variable domains of native heavy and light chains each comprise four FR regions, largely a adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies (see Kabat et al.). As used herein, numbering of immunoglobulin amino acid residues is done according to the immunoglobulin amino acid residue numbering system of Kabat et al., (Sequences of Proteins of Immunological Interest, National Institute of Health, Bethesda, Md. 1987), unless otherwise indicated.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 50-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues or CDR residues herein defined.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra; hinge region in constant domain of heavy chain is approximately residues 216-230 (EU numbering) of the heavy chain). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

The term "antibody fragment" refers to a portion of a full-length antibody, generally the target binding or variable region. Examples of antibody fragments include Fab, Fab', F(ab')$_2$ and Fv fragments. The phrase "functional fragment or analog" of an antibody is a compound having qualitative biological activity in common with a full-length antibody. For example, a functional fragment or analog of an anti-human Factor D antibody is one which can bind to Factor D in such a manner so as to prevent or substantially reduce the complement activation. As used herein, "functional fragment" with respect to antibodies, refers to Fv, F(ab) and F(ab')$_2$ fragments. An "Fv" fragment is the minimum antibody fragment which contains a complete target recognition and binding site. This region consists of a dimer of one heavy and one light chain variable domain in a tight, non-covalent association ($V_H$-$V_L$ dimer). It is in this configuration that the three CDRs of each variable domain interact to define an target binding site on the surface of the $V_H$-$V_L$ dimer. Collectively, the six CDRs confer target binding specificity to the antibody. However, even a single variable domain (or half of an Fv comprising only three CDRs specific for an target) has the ability to recognize and bind target. "Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for target binding.

The Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single targetic site. Furthermore, in contrast to conventional (polyclonal) antibody preparations which typically include different antibodies directed against different determinants (epitopes), each monoclonal antibody is directed against a single determinant on the target. In addition to their specificity, monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies for use with the present invention may be isolated from phage antibody libraries using the well known techniques. The parent monoclonal antibodies to be used in accordance with the present invention may be made by the hybridoma method first described by Kohler and Milstein, Nature 256, 495 (1975), or may be made by recombinant methods.

"Humanized" forms of non-human (e.g. murine) antibodies are chimeric immunoglobulins, immunoglobulin chains or fragments thereof (such as Fv, Fab, Fab', F(ab')$_2$ or other target-binding subsequences of antibodies) which contain minimal sequence derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin template chosen.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522-525 (1986); Riechmann et al., *Nature,* 332:323-327 (1988); Verhoeyen et al., *Science,* 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies can in some instances be important to reduce antigenicity and/or HAMA response (human anti-mouse antibody) when the antibody is intended for human therapeutic use. Reduction or elimination of a HAMA response is generally a significant aspect of clinical development of suitable therapeutic agents. See, e.g., Khaxzaeli et al., J. Natl. Cancer Inst. (1988), 80:937; Jaffers et al., Transplantation (1986), 41:572; Shawler et al., J. Immunol. (1985), 135:1530; Sears et al., J. Biol. Response Mod. (1984), 3:138; Miller et al., Blood (1983), 62:988; Hakimi et al., J. Immunol. (1991), 147:1352; Reichmann et al., Nature (1988), 332:323; Junghans et al., Cancer Res. (1990), 50:1495. As described herein, the invention provides antibodies that are humanized such that HAMA response is reduced or eliminated. Variants of these antibodies can further be obtained using routine methods known in the art, some of which are further described below. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.,* 196: 901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.* 151:2623 (1993)).

For example, an amino acid sequence from an antibody as described herein can serve as a starting (parent) sequence for diversification of the framework and/or hypervariable sequence(s). A selected framework sequence to which a starting hypervariable sequence is linked is referred to herein as an acceptor human framework. While the acceptor human frameworks may be from, or derived from, a human immunoglobulin (the VL and/or VH regions thereof), the acceptor human frameworks may be from, or derived from, a human consensus framework sequence as such frameworks have been demonstrated to have minimal, or no, immunogenicity in human patients. An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. In one embodiment, the VH acceptor human framework is identical in sequence to the VH human immunoglobulin framework sequence or human consensus framework sequence. In one embodiment, the VL acceptor human framework is identical in sequence to the VL human immunoglobulin framework sequence or human consensus framework sequence. A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor. The acceptor human framework may be from or derived from human antibody germline sequences available in the public databases.

In one embodiment, human consensus frameworks herein are from, or derived from, VH subgroup VII and/or VL kappa subgroup I consensus framework sequences.

In one embodiment, the human framework template used for generation of an anti-Factor D antibody may comprise framework sequences from a template comprising a combination of VI-4.1 b+ (VH7 family) and JH4d for VH chain (FIG. 3) and/or a combination of DPK4 (VκI family) and JK2 for VL chain (FIG. 4).

Thus, the VH acceptor human framework may comprise one, two, three or all of the following framework sequences: FR1 comprising QX$_1$QLVQSGX$_2$ELKKPGASVKVSCKAS (amino acids 1-25 of SEQ ID NO: 27), wherein X$_1$ is I or V, X$_2$ is P or S; FR2 comprising WVX$_3$QAPGQGLE (amino acids 36-46 of SEQ ID NO: 27), wherein X$_3$ is K or R; FR3 comprising RFVFSLDTSVSTAYLQISSLKAEDTAX$_4$YYCX$_5$R (amino acids 67-98 of SEQ ID NO: 27), wherein X$_4$ is T or V, X$_5$ is E or A; FR4 comprising WGQGTLVTVSS (amino acids 105-115 of SEQ ID NO: 8 or amino acids 105-115 of SEQ ID NO: 27)

Examples of VH consensus frameworks include:
human VH subgroup I consensus framework minus Kabat CDRs (SEQ ID NO: 28);
human VH subgroup I consensus framework minus extended hypervariable regions (SEQ ID NOs: 29-31);
human VH subgroup II consensus framework minus Kabat CDRs (SEQ ID NO: 32);
human VH subgroup II consensus framework minus extended hypervariable regions (SEQ ID NOs: 33-35);
human VH subgroup III consensus framework minus Kabat CDRs (SEQ ID NO: 36);

human VH subgroup III consensus framework minus extended hypervariable regions (SEQ ID NO: 37-39);
human VH subgroup VII consensus framework minus Kabat CDRs (SEQ ID NO: 55);
human VH subgroup VII consensus framework minus extended hypervariable regions (SEQ ID NO: 56-58);
human VH acceptor framework minus Kabat CDRs (SEQ ID NO: 40);
human VH acceptor framework minus extended hypervariable regions (SEQ ID NOs: 41-42);
human VH acceptor 2 framework minus Kabat CDRs (SEQ ID NO: 43); or
human VH acceptor 2 framework minus extended hypervariable regions (SEQ ID NOs: 44-45).

In one embodiment, the VH acceptor human framework comprises one, two, three or all of the following framework sequences:
FR1 comprising QVQLVQSGPELKKPGASVKVSCKAS (amino acids 1-25 of SEQ ID NO: 8),
FR2 comprising WVRQAPGQGLE (amino acids 67-97 of SEQ ID NO: 8),
FR3 comprising RFVFSLDTSVSTAYLQISSLKAEDTAVYYCER (amino acids 67-98 of SEQ ID NO: 8), RSVFSLDTSVSTAYLQISSLKAEDTAVYYCE (amino acids 67-97 of SEQ ID NO: 8), RFVFSLDTSVSTAYLQISSLKAEDTAVYYC (amino acids 67-96 of SEQ ID NO: 8), RFVFSLDTSVSTAYLQISSLKAEDTAVYYCS (SEQ ID NO: 51), or RFVFSLDTSVSTAYLQISSLKAEDTAVYYCSR (SEQ ID NO: 52)
FR4 comprising WGQGTLVTVSS (amino acids 105-115 of SEQ ID NO: 8 or amino acids 105-115 of SEQ ID NO: 27).

The VL acceptor human framework may comprise one, two, three or all of the following framework sequences:
FR1 comprising DIQX$_6$TQSPSSLSX$_7$SVGDRVTITC (amino acids 1-23 of SEQ ID NO: 26), wherein X$_6$ is V or M, X$_7$ is M or A;
FR2 comprising WYQQKPGKX$_8$PKLLIX$_9$ (amino acids 35-49 of SEQ ID NO: 26), wherein X$_8$ is P or V, X$_9$ is S or Y;
FR3 comprising GVPSRFSX$_{10}$SGSGX$_{11}$DFTLTISSLQPEDVATYYC (amino acids 57-88 of SEQ ID NO: 26), wherein X$_{10}$ is S or G, X$_{11}$ is A or T;
FR4 comprising FGQGTKX$_{12}$EIK (SEQ ID NO: 54), wherein X$_{12}$ is V or L.

Examples of VL consensus frameworks include:
human VL kappa subgroup I consensus framework (SEQ ID NO: 47);
human VL kappa subgroup II consensus framework (SEQ ID NO: 48);
human VL kappa subgroup III consensus framework (SEQ ID NO: 49); or
human VL kappa subgroup IV consensus framework (SEQ ID NO: 50)

In one embodiment, the VL acceptor human framework may comprise one, two, three or all of the following framework sequences:
FR1 comprising DIQVTQSPSSLSASVGDRVTITC (amino acids 1-23 of SEQ ID NO: 7),
FR2 comprising WYQQKPGKVPKLLIS (amino acids 35-49 of SEQ ID NO: 7),
FR3 comprising GVPSRFSGSGSGTDFTLTSSLQPEDVATYYC (amino acids 57-88 of SEQ ID NO: 7),
FR4 comprising FGQGTKLEIK (amino acids 98-107 of SEQ ID NO: 7), or FGQGTKVEIK (SEQ ID NO: 53).

While the acceptor may be identical in sequence to the human framework sequence selected, whether that be from a human immunoglobulin or a human consensus framework, the present invention contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

Hypervariable region residues of the non-human antibody are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-34 (L1), 50-56 (L2) and 89-97 (L3), 26-35 (H1), 50-65 or 49-65 (H2) and 93-102, 94-102, or 95-102 (H3).

In one aspect, the invention provides an antibody comprising at least one, two, three, four, five or six HVRs selected from (a) an HVR-H1 comprising the amino acid sequence selected from SEQ ID NO: 13 and SEQ ID NO:25; (b) an HVR-H2 comprising the amino acid sequence of SEQ ID NO: 14; (c) an HVR-H3 comprising the amino acid sequence selected from SEQ ID NO: 15 and SEQ ID NO: 20; (d) an HVR-L1 comprising the amino acid sequence of SEQ ID NO: 16; (e) an HVR-L2 comprising the amino acid sequence selected from SEQ ID NO: 17, SEQ ID NO: 21 and SEQ ID NO: 24; and (f) an HVR-L3 comprising the amino acid sequence selected from SEQ ID NO: 18, SEQ ID NO: 22 and SEQ ID NO: 19.

In one aspect, the invention provides an anti-Factor D antibody comprising at least one, two, three, four, five or six HVRs selected from (a) an HVR-H1 comprising an amino acid sequence having at least 90%, 91%, 92%, 93%, 94%, 95%, 96%, 97%, 98% or 99% sequence identity to an amino acid sequence selected from SEQ ID NO: 13 and SEQ ID NO: 25; (b) an HVR-H2 comprising an amino acid sequence having at least 90%, 91%, 92%, 93%, 94%, 95%, 96%, 97%, 98% or 99% sequence identity to an amino acid sequence of SEQ ID NO: 14; (c) an HVR-H3 comprising an amino acid sequence having at least 90%, 91%, 92%, 93%, 94%, 95%, 96%, 97%, 98% or 99% sequence identity to an amino acid sequence selected from SEQ ID NO: 15 and SEQ ID NO: 20; (d) an HVR-L1 comprising an amino acid sequence having at least 90%, 91%, 92%, 93%, 94%, 95%, 96%, 97%, 98% or 99% sequence identity to an amino acid sequence of SEQ ID NO: 16; (e) an HVR-L2 comprising an amino acid sequence having at least 90%, 91%, 92%, 93%, 94%, 95%, 96%, 97%, 98% or 99% sequence identity to an amino acid sequence selected from SEQ ID NO: 17, SEQ ID NO: 21 and SEQ ID NO: 24; and (f) an HVR-L3 comprising an amino acid sequence having at least 90%, 91%, 92%, 93%, 94%, 95%, 96%, 97%, 98% or 99% sequence identity to an amino acid sequence selected from SEQ ID NO: 18, SEQ ID NO: 22 and SEQ ID NO: 19. In some embodiments, an HVR having an amino acid sequence having at least 90%, 91%, 92%, 93%, 94%, 95%, 96%, 97%, 98% or 99% sequence identity contains substitutions, insertions, or deletions relative to the reference sequence, but an antibody comprising that amino acid sequence retains the ability to bind to Factor D. In some embodiments, a total of 1 to 10 amino acids have been substituted, inserted, or deleted in the reference sequence selected from the group consisting of SEQ ID NO: 13, SEQ ID NO: 25, SEQ ID NO: 14, SEQ ID NO: 15, SEQ ID NO: 20, SEQ ID NO: 16, SEQ ID NO: 17, SEQ ID NO; 21, SEQ ID NO: 23, SEQ ID NO: 18, SEQ ID NO: 22 and SEQ ID NO: 24. In some embodiments, the invention provides an antibody comprising at least one, two, three, four, five or six HVRs selected from (a) an HVR-H1 comprising the amino acid sequence selected from SEQ ID NO: 13 and SEQ ID NO: 25; (b) an HVR-H2 comprising the amino acid sequence of SEQ ID NO: 14; (c) an HVR-H3 comprising the amino acid sequence selected from SEQ ID NO: 15 and SEQ ID NO: 20; (d) an HVR-L1 comprising the amino acid sequence of SEQ ID NO: 16; (e) an HVR-L2 comprising the amino acid sequence selected from SEQ ID NO: 17, SEQ ID NO: 21 and SEQ ID NO:24; and (f) an HVR-L3 comprising the amino acid sequence selected from SEQ ID NO: 18, SEQ ID NO: 22 and SEQ ID NO: 19.

In one aspect, the invention provides an antibody comprising a heavy chain variable domain selected from SEQ ID NO: 6, SEQ ID NO: 8, SEQ ID NO: 10, SEQ ID NO: 12. In one aspect, the invention provides an antibody comprising a light chain variable domain selected from SEQ ID NO: 5, SEQ ID NO: 7, SEQ ID NO: 9 and SEQ ID NO: 11. In one aspect, the invention provides an antibody comprising a heavy chain variable domain comprising SEQ ID NO: 6. In one aspect, the invention provides an antibody comprising a light chain variable domain comprising SEQ ID NO: 5. In one aspect, the invention provides an antibody comprising a heavy chain variable domain comprising SEQ ID NO: 6 and a light chain variable domain comprising SEQ ID NO: 5. In one aspect, the invention provides an antibody comprising a heavy chain variable domain comprising SEQ ID NO: 8. In one aspect, the invention provides an antibody comprising a light chain variable domain comprising SEQ ID NO: 7. In one aspect, the invention provides an antibody comprising a heavy chain variable domain comprising SEQ ID NO: 8 and a light chain variable domain comprising SEQ ID NO: 7. In one aspect, the invention provides an antibody comprising a heavy chain variable domain comprising SEQ ID NO: 10. In one aspect, the invention provides an antibody comprising a light chain variable domain comprising SEQ ID NO: 9. In one aspect, the invention provides an antibody comprising a heavy chain variable domain comprising SEQ ID NO: 10 and a light chain variable domain comprising SEQ ID NO: 9. In one aspect, the invention provides an antibody comprising a heavy chain variable domain comprising SEQ ID NO: 12. In one aspect, the invention provides an antibody comprising a light chain variable domain comprising SEQ ID NO: 11. In one aspect, the invention provides an antibody comprising a heavy chain variable domain comprising SEQ ID NO: 12 and a light chain variable domain comprising SEQ ID NO: 11.

In one aspect, the invention provides an anti-Factor D antibody comprising a heavy chain variable domain comprising an amino acid sequence having at least 90%, 91%, 92%, 93%, 94%, 95%, 96%, 97%, 98% or 99% sequence identity to an amino acid sequence selected from the group consisting of SEQ ID NO: 6, 8, 10 and 12. In some embodiments, an amino acid sequence having at least 90%, 91%, 92%, 93%, 94%, 95%, 96%, 97%, 98% or 99% sequence identity contains substitutions, insertions, or deletions relative to the reference sequence, but an antibody comprising that amino acid sequence retains the ability to bind to Factor D. In some embodiments, a total of 1 to 10 amino acids have been substituted, inserted, or deleted in a sequence selected from the group consisting of SEQ ID NO: 6, 8, 10 and 12. In some embodiments, the substitutions, insertions or deletions occur in regions outside the HVRs (i.e., in the FRs). In some embodiments, an anti-Factor D antibody comprises a heavy chain variable domain comprising an amino acid sequence selected from the group consisting of SEQ ID NO: 6, 8, 10 or 12.

In some embodiments, the invention provides an anti-Factor D antibody comprising a light chain variable domain comprising an amino acid sequence having at least 90%, 91%, 92%, 93%, 94%, 95%, 96%, 97%, 98% or 99% sequence identity to an amino acid sequence selected from the group consisting of SEQ ID NO: 5, 7, 9 and 11. In some embodiments, an amino acid sequence having at least 90%, 91%, 92%, 93%, 94%, 95%, 96%, 97%, 98% or 99% sequence identity contains substitutions, insertions, or deletions relative to the reference sequence, but an antibody comprising that amino acid sequence retains the ability to bind to Factor D. In some embodiments, a total of 1 to 10 amino acids have been substituted, inserted, or deleted in a sequence selected from the group consisting of SEQ ID NO: 5, 7, 9 and 11. In some embodiments, the substitutions, insertions or deletions occur in regions outside the HVRs (i.e., in the FRs). In some embodiments, an anti-Factor D antibody comprises a light chain variable domain comprising an amino acid sequence selected from the group consisting of SEQ ID NO: 5, 7, 9 and 11.

An anti-Factor D antibody may comprise any suitable framework variable domain sequence, provided that the antibody retains the ability to bind Factor D. For example, in some embodiments, anti-Factor D antibodies of the invention comprise a heavy chain variable domain framework sequence that is a combination of VI.4.1 b+ and JH4d (See FIG. 3). In some embodiments, anti-Factor D antibodies of the invention comprise a human subgroup VII heavy chain framework consensus sequence. In some embodiments, anti-Factor D antibodies of the invention comprise a heavy chain variable domain framework sequence comprising FR1 comprising amino acids 1-25 of SEQ ID NO: 8, FR2 comprising amino acids 36-46 of SEQ ID NO: 8, FR3 comprising amino acids 67-98 of SEQ ID NO: 8 and FR4 comprising amino acids 105-115 of SEQ ID NO: 8 In one embodiment of these antibodies, the heavy chain variable domain sequence comprises substitution(s) at position 40 and/or 88 (Kabat numbering). In one embodiment of these antibodies, position 40 is cysteine (C) or alanine (A) and/or position 88 is cysteine (C) or alanine (A). In some embodiments, anti-Factor D antibodies of the invention comprise a light chain variable domain framework sequence that is a combination of DPK4 and JK2 (See FIG. 4). In some embodiments, anti-Factor D antibodies of the invention comprise a human kappa I (κI) light chain framework consensus sequence. In some embodiments, anti-Factor D antibodies of the invention comprise a light chain variable domain framework sequence comprising FR1 comprising amino acids 1-23 of SEQ ID NO: 7, FR2 comprising amino acids 35-49 of SEQ ID NO: 7, FR3 comprising amino acids 57-88 of SEQ ID NO: 7 and FR4 comprising amino acids 98-107 of SEQ ID NO: 7. In one embodiment of these antibodies, the light chain variable framework sequence comprises one or more substitution(s) at position 15, 43 and/or 104 (Kabat numbering). In one embodiment of these antibodies, position 15 is cysteine (C) or valine (V), position 43 is cysteine (C) or alanine (A) and/or position 104 is valine (V) or leucine (L).

Further, an anti-Factor D antibody may comprise any suitable constant domain sequence, provided that the antibody retains the ability to bind Factor D. For example, in some embodiments, anti-Factor D antibodies of the invention comprise at least a portion of a heavy chain constant domain. In one embodiment, anti-Factor D antibodies of the invention comprise a heavy chain constant domain of either one or a combination of an α, δ, ε, γ, or μ heavy chain. Depending on the amino acid sequence of the constant domain of their heavy chains (C$_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in C$_H$ sequence and function, e.g., humans express the following subclasses: IgG1, IgG2, IgG3, IgG4, IgA1, and IgA2. In one embodiment, anti-Factor D antibodies of the invention comprise a heavy chain constant domain comprising substitutions at amino acid positions that results in a desired effect on effector function (e.g. binding affinity). In one embodiment, anti-Factor D antibodies of the invention comprise a heavy chain constant domain comprising substitutions at amino acid positions that do not result in an effect on effector function (e.g. binding affinity). In one embodiment, anti-Factor D antibodies of the invention comprise a heavy chain constant domain of the IgG type (e.g. IgG1, IgG2, IgG3 or IgG4) and further comprise a substitution at position 114 (Kabat numbering; equivalent to 118 in EU numbering), 168 (Kabat numbering; equivalent to 172 in EU numbering), 172 (Kabat numbering; equivalent to 176 in EU numbering) and/or 228 (EU numbering). In one embodiment, anti-Factor D antibodies of the invention comprise a heavy chain constant domain of the IgG (e.g. IgG1, IgG2, IgG3 or IgG4) type and further comprise a substitution at position 114 wherein position 114 is a cysteine (C) or alanine (A), position 168 is cysteine (C) or alanine (A), position 172 is a cysteine (C) or alanine (A) and/or position 228 is a proline (P), arginine (R) or serine (S).

Further, for example, in some embodiments, anti-Factor D antibodies of the invention comprise at least a portion of a light chain constant domain. In one embodiment, anti-Factor D antibodies of the invention comprise a light chain constant domain of either one or a combination of a kappa or a lambda light chain, as the light chain from any vertebrate species can be assigned to one of two clearly distinct types, called kappa and lambda, based on the amino acid sequences of their constant domains. In one embodiment, anti-Factor D antibodies of the invention comprise a light chain constant domain comprising substitutions at amino acid positions that results in a desired effect on effector function (e.g. binding affinity). In one embodiment, anti-Factor D antibodies of the invention comprise a light chain constant domain comprising substitutions at amino acid positions that do not result in an effect on effector function (e.g., binding affinity). In one embodiment, anti-Factor D antibodies of the invention comprise a light chain constant domain of the kappa type and further comprise a substitution at position 110, 144, 146 and/or 168 (Kabat numbering). In one embodiment, anti-Factor D antibodies of the invention comprise a light chain constant domain of the kappa type and further comprise a substitution at position 110 wherein 110 is a cysteine (C) or valine (V), at position 144 wherein 144 is a cysteine (C) or alanine (A), at position 146 wherein 146 is a isoleucine (I) or valine (V) and/or at position 168 wherein 168 is a cysteine (C) or serine (S).

In one aspect, the invention provides antibodies that compete with murine antibody 166-32 and/or humanized anti-Factor D antibody clone #56, #111, #250 or #416, and/or an antibody comprising variable domain or HVR sequences of humanized anti-Factor D antibody clone #56, #111, #250 or #416. Antibodies that bind to the same epitope as murine antibody 166-32 and/or humanized anti-Factor D antibody clone #56, #111, #250 or #416, and/or an antibody compris-ing variable domain or HVR sequences of humanized anti-Factor D antibody clone #56, #111, #250 or #416 are also provided.

In one embodiment, the invention provides an anti-Factor D antibody wherein the monovalent affinity of the antibody to Factor D (e.g., affinity of the antibody as a Fab fragment to Factor D) is lower, for example at least 1-fold or 2-fold lower than the monovalent affinity of a chimeric antibody (e.g. affinity of the cihmeric antibody as a Fab fragment to Factor D), comprising, consisting or consisting essentially of a light chain variable domain of SEQ ID NO: 2 and heavy chain variable domain of SEQ ID NO: 1.

In one embodiment, the invention provides an anti-Factor D antibody wherein the bivalent affinity of the antibody to Factor D (e.g., affinity of the antibody as an IgG to Factor D) is lower, for example at least 1-fold or 2-fold lower than the bivalent affinity of a chimeric antibody (e.g. affinity of the cihmeric antibody as an IgG to Factor D), comprising, consisting or consisting essentially of a light chain variable domain of SEQ ID NO: 2 and heavy chain variable domain of SEQ ID NO: 1.

In another embodiment, the invention provides an anti-Factor D antibody wherein the monovalent affinity of the antibody to Factor D (e.g., affinity of the antibody as a Fab fragment to Factor D) is greater, for example at least 1-fold or 2-fold greater than the monovalent affinity of a chimeric antibody (e.g. affinity of the chimeric antibody as a Fab fragment to Factor D), comprising, consisting or consisting essentially of a light chain variable domain of SEQ ID NO: 2 and heavy chain variable domain of SEQ ID NO: 1.

In another embodiment, the invention provides an anti-Factor D antibody wherein the bivalent affinity of the antibody to Factor D (e.g., affinity of the antibody as an IgG to Factor D) is greater, for example at least 1-fold or 2-fold greater than the bivalent affinity of a chimeric antibody (e.g. affinity of the chimeric antibody as an IgG to Factor D), comprising, consisting or consisting essentially of a light chain variable domain of SEQ ID NO: 2 and heavy chain variable domain of SEQ ID NO: 1.

In another embodiment, the invention provides an anti-Factor D antibody wherein the affinity of the antibody in its monovalent form to Factor D (e.g., affinity of the antibody as a Fab fragment to Factor D) is 1.0 nM ($1.0 \times 10^{-9}$ M) or better. In another embodiment, the invention provides an anti-Factor D antibody wherein the affinity of the antibody in its monovalent form to Factor D (e.g., affinity of the antibody as a Fab fragment to Factor D) is 0.5 nM ($0.5 \times 10^{-9}$ M) or better. In another embodiment, the invention provides an anti-Factor D antibody wherein the affinity of the antibody in its monovalent form to Factor D (e.g., affinity of the antibody as a Fab fragment to Factor D) is 1.0 pM ($1.0 \times 10^{-12}$ M) or better. In another embodiment, the invention provides an anti-Factor D antibody wherein the affinity of the antibody in its monovalent form to Factor D (e.g., affinity of the antibody as a Fab fragment to Factor D) is 0.5 pM ($0.5 \times 10^{-12}$ M) or better.

In another embodiment, the invention provides an anti-Factor D antibody wherein the affinity of the antibody in its bivalent form to Factor D (e.g., affinity of the antibody as an IgG to Factor D) is 1.0 nM ($1.0 \times 10^{-9}$ M) or better. In another embodiment, the invention provides an anti-Factor D antibody wherein the affinity of the antibody in its bivalent form to Factor D (e.g., affinity of the antibody as an IgG to Factor D) is 0.5 nM ($0.5 \times 10^{-9}$ M) or better. In another embodiment, the invention provides an anti-Factor D antibody wherein the affinity of the antibody in its bivalent form to Factor D (e.g., affinity of the antibody as an IgG to Factor D) is 1.0 pM ($1.0 \times 10^{-12}$ M) or better. In another embodiment, the invention provides an anti-Factor D antibody wherein the affinity of the antibody in its bivalent form to Factor D (e.g., affinity of the antibody as an IgG to Factor D) is 0.5 pM ($0.5\times10^{-12}$ M) or better.

In another embodiment, the invention provides an anti-Factor D antibody wherein the affinity of the antibody in its monovalent form to Factor D (e.g., affinity of the antibody as a Fab fragment to Factor D) is between 0.5 mM ($0.5\times10^{-6}$ M) and 0.5 pM ($0.5\times10^{-12}$ M). In another embodiment, the invention provides an anti-Factor D antibody wherein the affinity of the antibody in its monovalent form to Factor D (e.g., affinity of the antibody as a Fab fragment to Factor D) is between 15 nM ($15\times10^{-9}$ M) and 0.1 nM ($0.1\times10^{-9}$ M). In another embodiment, the invention provides an anti-Factor D antibody wherein the affinity of the antibody in its monovalent form to Factor D (e.g., affinity of the antibody as a Fab fragment to Factor D) is between 5.5 nM ($5.5\times10^{-9}$ M) and 1 nM ($1\times0-9$ M). In another embodiment, the invention provides an anti-Factor D antibody wherein the affinity of the antibody in its monovalent form to Factor D (e.g., affinity of the antibody as a Fab fragment to Factor D) is between 0.5 pM ($0.5\times10^{-12}$ M) and 2 pM ($2\times10^{-12}$ M).

In another embodiment, the invention provides an anti-Factor D antibody wherein the affinity of the antibody in its bivalent form to Factor D (e.g., affinity of the antibody as an IgG to Factor D) is between 0.5 mM ($0.5\times10^{-6}$ M) and 0.5 pM ($0.5\times10^{-12}$ M). In another embodiment, the invention provides an anti-Factor D antibody wherein the affinity of the antibody in its bivalent form to Factor D (e.g., affinity of the antibody as an IgG to Factor D) is between 10 nM ($10\times0-9$ M) and 0.05 nM ($0.05\times10^{-9}$ M). In another embodiment, the invention provides an anti-Factor D antibody wherein the affinity of the antibody in its bivalent form to Factor D (e.g., affinity of the antibody as an IgG to Factor D) is between 5.5 nM ($5.5\times10^{-9}$ M) and 1 nM ($1\times10^{-9}$ M). In another embodiment, the invention provides an anti-Factor D antibody wherein the affinity of the antibody in its bivalent form to Factor D (e.g., affinity of the antibody as an IgG to Factor D) is between 0.5 pM ($0.5\times10^{-12}$ M) and 2 pM ($2\times10^{-12}$ M).

In another embodiment, the invention provides an anti-Factor D antibody wherein the affinity of the antibody in its monovalent form to Factor D (e.g., affinity of the antibody as a Fab fragment to Factor D) is about 0.37 nM ($3.7\times10^{-10}$ M). In another embodiment, the invention provides an anti-Factor D antibody wherein the affinity of the antibody in its monovalent form to Factor D (e., affinity of the antibody as a Fab fragment to Factor D) is about 0.33 nM ($3.3\times10^{-10}$ M). In another embodiment, the invention provides an anti-Factor D antibody wherein the affinity of the antibody in its monovalent form to Factor D (e.g., affinity of the antibody as a Fab fragment to Factor D) is about 0.51 nM ($5.1\times10^{-10}$ M). In another embodiment, the invention provides an anti-Factor D antibody wherein the affinity of the antibody in its monovalent form to Factor D (e.g., affinity of the antibody as a Fab fragment to Factor D) is about 2.7 nM ($2.7\times10^{-9}$ M). In another embodiment, the invention provides an anti-Factor D antibody wherein the affinity of the antibody in its monovalent form to Factor D (e.g., affinity of the antibody as a Fab fragment to Factor D) is about 1.4 nM ($1.4\times10^{-9}$ M). In another embodiment, the invention provides an anti-Factor D antibody wherein the affinity of the antibody in its monovalent form to Factor D (e.g., affinity of the antibody as a Fab fragment to Factor D) is about 1.4 pM ($1.4\times10^{-12}$ M). In another embodiment, the invention provides an anti-Factor D antibody wherein the affinity of the antibody in its bivalent form to Factor D (e.g., affinity of the antibody as a IgG to Factor D) is about 1.1 pM ($1.1\times10^{12}$ M). In another embodiment, the invention provides an anti-Factor D antibody wherein the affinity of the antibody in its monovalent form to Factor D (e.g., affinity of the antibody as a Fab fragment to Factor D) is about 0.19 nM ($0.19\times10^{-9}$ M). In another embodiment, the invention provides an anti-Factor D antibody wherein the affinity of the antibody in its bivalent form to Factor D (e.g., affinity of the antibody as a IgG to Factor D) is about 0.08 nM ($0.08\times10^{-9}$ M). In another embodiment, the invention provides an anti-Factor D antibody wherein the affinity of the antibody in its monovalent form to Factor D (e.g., affinity of the antibody as a Fab fragment to Factor D) is about 12.3 nM ($12.3\times10^{-9}$ M). In another embodiment, the invention provides an anti-Factor D antibody wherein the affinity of the antibody in its bivalent form to Factor D (e.g., affinity of the antibody as a IgG to Factor D) is about 9.0 nM ($9.0\times10^{-9}$ M).

In another embodiment, the invention provides an anti-Factor D antibody wherein the affinity of the antibody in its monovalent form to Factor D (e.g., affinity of the antibody as a Fab fragment to Factor D) is about 1.4 pM ($1.4\times10^{-12}$ M)+/−0.5. In another embodiment, the invention provides an anti-Factor D antibody wherein the affinity of the antibody in its bivalent form to Factor D (e.g., affinity of the antibody as an IgG to Factor D) is about 1.1 pM ($1.1\times10^{-12}$ M)+/−0.6. In another embodiment, the invention provides an anti-Factor D antibody wherein the affinity of the antibody in its monovalent form to Factor D (e.g., affinity of the antibody as a Fab fragment to Factor D) is about 0.19 nM ($0.19\times10^{-9}$ M)+/−0.01. In another embodiment, the invention provides an anti-Factor D antibody wherein the affinity of the antibody in its bivalent form to Factor D (e.g., affinity of the antibody as a IgG to Factor D) is about 0.08 nM ($0.08\times10^{-9}$ M)+/−0.01. In another embodiment, the invention provides an anti-Factor D antibody wherein the affinity of the antibody in its monovalent form to Factor D (e.g., affinity of the antibody as a Fab fragment to Factor D) is about 12.3 nM ($12.3\times10^{-9}$ M)+/−2. In another embodiment, the invention provides an anti-Factor D antibody wherein the affinity of the antibody in its bivalent form to Factor D (e.g., affinity of the antibody as a IgG to Factor D) is about 9.0 nM ($9.0\times10^{-9}$ M)+/−1.

In another embodiment, an anti-Factor D antibody may have an affinity in its monovalent form to Factor D (e.g., affinity of the antibody as a Fab fragment to Factor D) of about 3.7 nM ($3.7\times10^{-9}$ M)+/−2. In another embodiment, an anti-Factor D antibody may have an affinity in its monovalent form to Factor D (e.g., affinity of the antibody as a Fab fragment to Factor D) of about 3.3 nM ($3.3\times10^{-9}$ M)+/−2. In another embodiment, an anti-Factor D antibody may have an affinity in its monovalent form to Factor D (e.g., affinity of the antibody as a Fab fragment to Factor D) of about 5.1 nM ($5.1\times10^{-9}$ M)+/−2. In another embodiment, an anti-Factor D antibody may have an affinity in its monovalent form to Factor D (e.g., affinity of the antibody as a Fab fragment to Factor D) of about 2.7 nM ($2.7\times10^{-9}$ M)+/−2. In another embodiment, an anti-Factor D antibody may have an affinity in its monovalent form to Factor D (e.g., affinity of the antibody as a Fab fragment to Factor D) of about 1.4 nM ($1.4\times10^{-9}$ M)+/−2. In another embodiment, an anti-Factor D antibody may have an affinity in its monovalent form to Factor D (e.g., affinity of the antibody as a Fab fragment to Factor D) of about 1.4 pM ($1.4\times10^{-12}$ M)+/−2. In another embodiment, an anti-Factor D antibody may have an affinity in its bivalent form to Factor D (e.g., affinity of the antibody as a IgG to Factor D) of about 1.1 pM ($1.1\times10^{-12}$ M)+/−2. In another embodiment, an anti-Factor D antibody may have an affinity in its monovalent form to Factor D (e.g., affinity of the antibody as a Fab fragment to Factor D) is about 0.19 nM (0.19×

$10^{-9}$ M)+/−2. In another embodiment, an anti-Factor D antibody may have an affinity in its bivalent form to Factor D (e.g., affinity of the antibody as a IgG to Factor D) is about 0.08 nM ($0.08\times10^{-9}$ M)+/−2. In another embodiment, an anti-Factor D antibody may have an affinity in its monovalent form to Factor D (e.g., affinity of the antibody as a Fab fragment to Factor D) is about 12.3 nM ($12.3\times10^{-9}$ M)+/−2. In another embodiment, an anti-Factor D antibody may have an affinity in its bivalent form to Factor D (e.g., affinity of the antibody as a IgG to Factor D) is about 9.0 nM ($9.0\times10^{-9}$ M)+/−2.

As is well-established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. As described in greater detail herein, fold difference in binding affinity can be quantified in terms of the ratio of the monovalent binding affinity value of a humanized antibody (e.g., in Fab form) and the monovalent binding affinity value of a reference/comparator antibody (e.g., in Fab form) (e.g., a murine antibody having donor hypervariable region sequences), wherein the binding affinity values are determined under similar assay conditions. Thus, in one embodiment, the fold difference in binding affinity is determined as the ratio of the Kd values of the humanized antibody in Fab form and said reference/comparator Fab antibody. For example, in one embodiment, if an antibody of the invention (A) has an affinity that is "3-fold lower" than the affinity of a reference antibody (M), then if the Kd value for A is 3×, the Kd value of M would be 1×, and the ratio of Kd of A to Kd of M would be 3:1. Conversely, in one embodiment, if an antibody of the invention (C) has an affinity that is "3-fold greater" than the affinity of a reference antibody (R), then if the Kd value for C is 1×, the Kd value of R would be 3×, and the ratio of Kd of C to Kd of R would be 1:3. Any of a number of assays known in the art, including those described herein, can be used to obtain binding affinity measurements, including, for example, Biacore, radioimmunoassay (RIA) and ELISA.

Further, Kd values for an antibody of the invention may vary depending on conditions of the particular assay used. For example, in one embodiment, binding affinity measurements may be obtained in an assay wherein the Fab or antibody is immobilized and binding of the ligand, i.e. Factor D, is measured or alternatively, the ligand, i.e. Factor D, for the Fab or antibody is immobilized and binding of the Fab or antibody is measured. In one embodiment, the binding affinity measurements may be obtained in an assay wherein the regeneration conditions may comprise (1) 10 mM glycein or 4M $MgCl_2$ at pH 1.5, and (2) pH between pH of 1.0 and pH of 7.5, including pH of 1.5, pH of 5.0, pH of 6.0 and pH of 7.2. In one embodiment, the binding affinity measurements may be obtained in an assay wherein the binding conditions may comprise (1) PBS or HEPES-buffered saline and (2) Tween-20, i.e. 0.1% Tween-20. In one embodiment, the binding affinity measurements may be obtained in an assay wherein the source of the ligand, i.e Factor D, may be from commercially available sources. In one embodiment, binding affinity measurements may be obtained in an assay wherein (1) the Fab or antibody is immobilized and binding of the ligand, i.e. Factor D is measured, (2) the regeneration conditions comprise 4M $MgCl_2$ at pH 7.2 and (3) the binding conditions comprise HEPES-buffered saline, pH 7.2 containing 0.1% Tween-20. In one embodiment, binding affinity measurements may be obtained in an assay wherein (1) the ligand, i.e. Factor D, is immobilized and binding of the Fab or antibody is measured, (2) the regeneration conditions comprise 10 mM glycine at pH 1.5 and (3) the binding conditions comprise PBS buffer.

The terms "cell", "cell line" and "cell culture" include progeny. It is also understood that all progeny may not be precisely identical in DNA content, due to deliberate or inadvertent mutations. Variant progeny that have the same function or biological property, as screened for in the originally transformed cell, are included. The "host cells" used in the present invention generally are prokaryotic or eukaryotic hosts.

The term "vector" means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may in some instances, integrate into the genome itself. In the present specification, "plasmid" and "vector" are sometimes used interchangeably, as the plasmid is the most commonly used form of vector. However, the invention is intended to include such other forms of vectors which serve equivalent function as and which are, or become, known in the art.

The word "label" when used herein refers to a detectable compound or composition which can be conjugated directly or indirectly to a molecule or protein, e.g., an antibody. The label may itself be detectable (e.g., radioisotope labels or fluorescent labels) or, in the case of an enzymatic label, may catalyze chemical alteration of a substrate compound or composition which is detectable.

As used herein, "solid phase" means a non-aqueous matrix to which the antibody of the present invention can adhere. Example of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column).

Generation of Antibodies
Selection and Transformation of Host Cells

Suitable host cells for cloning or expressing the DNA in the vectors herein are prokaryotic, yeast, or higher eukaryotic cells. Suitable prokaryotes for this purpose include both Gram-negative and Gram-positive organisms, for example, Enterobacteria such as *E. coli Enterobacter, Erwinia, Klebsiella, Proteus, Salmonella, Serratia*, and *Shigella*, as well as *Bacilli, Pseudomonas*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae* is the most commonly used among lower eukaryotic host microorganisms. However, a number of other genera, species, and strains are commonly available and useful herein, such as *Schizosaccharomyces pombe; Kluyveromyces; Candida; Trichoderma; Neurospora crassa*; and filamentous fungi such as e.g., *Neurospora, Penicillium, Tolypocladium,* and *Aspergillus* hosts, such as *A. nidulans* and *A. niger.*

Suitable host cells for the expression of glycosylated antibodies are derived from multicellular organisms. In principal, any higher eukaryotic cell culture is workable, whether from vertebrate or invertebrate culture. Examples of invertebrate cells include plant and insect cells, Luckow et al., Bio/Technology 6, 47-55 (1988); Miller et al., Genetic Engineering, Setlow et al. eds. Vol. 8, pp. 277-279 (Plenam publishing 1986); Mseda et al., Nature 315, 592-594 (1985). Numerous baculoviral strains and variants and corresponding permissive insect host cells from hosts such as *Spodoptera frugiperda* (caterpillar), *Aedes* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Moreover, plant cells cultures of cotton, corn, potato, soybean, petunia, tomato, and tobacco and also be utilized as hosts.

Vertebrate cells, and propagation of vertebrate cells, in culture (tissue culture) has become a routine procedure. See Tissue Culture, Academic Press, Kruse and Patterson, eds. (1973). Examples of useful mammalian host cell lines are monkey kidney; human embryonic kidney line; baby hamster kidney cells; Chinese hamster ovary cells/–DHFR (CHO, Urlaub et al., Proc. Natl. Acad. Sci. USA 77: 4216 (1980)); mouse sertoli cells; human cervical carcinoma cells (HELA); canine kidney cells; human lung cells; human liver cells; mouse mammary tumor; and NS0 cells.

Host cells are transformed with the above-described vectors for antibody production and cultured in conventional nutrient media modified as appropriate for inducing promoters, selecting transformants, or amplifying the genes encoding the desired sequences.

The host cells used to produce the antibody variant of this invention may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing host cells. In addition, any of the media described in Ham et al., Meth. Enzymol. 58: 44 (1979), Barnes et al., Anal. Biochem. 102: 255 (1980), U.S. Pat. No. 4,767,704; 4,657,866; 4,560,655; 5,122,469; 5,712,163; or 6,048,728 may be used as culture media for the host cells. Any of these media may be supplemented as necessary with hormones and/or other growth factors (such as insulin, transferrin, or epidermal growth factor), salts (such as X-chlorides, where X is sodium, calcium, magnesium; and phosphates), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Antibody Purification

When using recombinant techniques, the antibody can be produced intracellularly, in the periplasmic space, or directly secreted into the medium. If the antibody variant is produced intracellularly, as a first step, the particulate debris, either host cells or lysed fragments, may be removed, for example, by centrifugation or ultrafiltration. Carter et al., Bio/Technology 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody variant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel elecrophoresis, dialysis, and affinity chromatography, with affinity chromatography being the preferred purification technique. The suitability of protein A as an affinity ligand depends on the species and isotype of any immunoglobulin Fc domain that is present in the antibody variant. Protein A can be used to purify antibodies that are based on human IgG1, IgG2 or IgG4 heavy chains (Lindmark et al., J. Immunol. Meth. 62: 1-13 (1983)). Protein G is recommended for all mouse isotypes and for human IgG3 (Guss et al., EMBO J. 5: 1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody variant comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody variant to be recovered.

Following any preliminary purification step(s), the mixture comprising the antibody variant of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations

Therapeutic formulations of the polypeptide or antibody may be prepared for storage as lyophilized formulations or aqueous solutions by mixing the polypeptide having the desired degree of purity with optional "pharmaceutically-acceptable" carriers, excipients or stabilizers typically employed in the art (all of which are termed "excipients"). For example, buffering agents, stabilizing agents, preservatives, isotonifiers, non-ionic detergents, antioxidants and other miscellaneous additives. (See Remington's Pharmaceutical Sciences, 16th edition, A. Osol, Ed. (1980)). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives may be added to retard microbial growth, and may be added in amounts ranging from 0.2%-1% (w/v). Suitable preservatives for use with the present invention include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, alkyl parabens such as methyl or propyl paraben, catechol, resorcinol, cyclohexanol, and 3-pentanol.

Isotonicifiers sometimes known as "stabilizers" may be added to ensure isotonicity of liquid compositions of the present invention and include polhydric sugar alcohols, preferably trihydric or higher sugar alcohols, such as glycerin, erythritol, arabitol, xylitol, sorbitol and mannitol.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, .alpha.-monothioglycerol and sodium thio sulfate; low molecular weight polypeptides (i.e. <10 residues); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccharides such as raffinose; polysaccharides such as dextran. Stabilizers may be present in the range from 0.1 to 10,000 weights per part of weight active protein.

Non-ionic surfactants or detergents (also known as "wetting agents") may be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), poloxamers (184, 188 etc.), Pluronic® polyols, polyoxyethylene sorbitan monoethers (Tween®-20, Tween®-80, etc.). Non-ionic surfactants may be present in a range of about 0.05 mg/ml to about 1.0 mg/ml, preferably about 0.07 mg/ml to about 0.2 mg/ml.

Additional miscellaneous excipients include bulking agents, (e.g. starch), chelating agents (e.g. EDTA), antioxidants (e.g., ascorbic acid, methionine, vitamin E), and cosolvents. The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended. The active ingredients may also be entrapped in microcapsule prepared, for example, by coaservation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, A. Osal, Ed. (1980).

The formulations to be used for in vivo administration must be sterile. This is readily accomplished, for example, by filtration through sterile filtration membranes. Sustained-release preparations may be prepared. Suitable examples of sustained-release preparations include semi-permeable matrices of solid hydrophobic polymers containing the antibody variant, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C. resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The amount of therapeutic polypeptide, antibody or fragment thereof which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans.

In a preferred embodiment, an aqueous solution of therapeutic polypeptide, antibody or fragment thereof is administered by subcutaneous injection. Each dose may range from about 0.5 μg to about 50 μg per kilogram of body weight, or more preferably, from about 3 μg to about 30 μg per kilogram body weight.

The dosing schedule for subcutaneous administration may vary form once a month to daily depending on a number of clinical factors, including the type of disease, severity of disease, and the subject's sensitivity to the therapeutic agent.

Uses for the Humanized Antibody

The humanized antibodies of the present invention are useful in diagnostic assays, e.g., for detecting expression of a target of interest in specific cells, tissues, or serum. For diagnostic applications, the antibody variant typically will be labeled with a detectable moiety. Numerous labels are available. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzym. (Ed. J. Langone & H. Van Vunakis), Academic press, New York, 73: 147-166 (1981).

Sometimes, the label is indirectly conjugated with the antibody variant. The skilled artisan will be aware of various techniques for achieving this. For example, the antibody variant can be conjugated with biotin and any of the three broad categories of labels mentioned above can be conjugated with avidin, or vice versa. Biotin binds selectively to avidin and thus, the label can be conjugated with the antibody variant in this indirect manner. Alternatively, to achieve indirect conjugation of the label with the antibody variant, the antibody variant is conjugated with a small hapten (e.g. digloxin) and one of the different types of labels mentioned above is conjugated with an anti-hapten antibody variant (e.g. anti-digloxin antibody). Thus, indirect conjugation of the label with the antibody variant can be achieved.

In another embodiment of the invention, the antibody variant need not be labeled, and the presence thereof can be detected using a labeled antibody which binds to the antibody variant.

The antibodies of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

Competitive binding assays rely on the ability of a labeled standard to compete with the test sample for binding with a limited amount of antibody variant. The amount of target in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies may conveniently be separated from the standard and test sample which remain unbound.

Sandwich assays involve the use of two antibodies, each capable of binding to a different immunogenic portion, or epitope, or the protein to be detected. In a sandwich assay, the test sample to be analyzed is bound by a first antibody which is immobilized on a solid support, and thereafter a second antibody binds to the test sample, thus forming an insoluble three-part complex. See e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Generally, the antibody variant is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. For example, a high affinity anti-IgE antibody of the present invention may be used to detect the amount of IgE present in, e.g., the lungs of an asthmatic patient.

The antibody of the present invention can be provided in a kit, i.e., packaged combination of reagents in predetermined amounts with instructions for performing the diagnostic assay. Where the antibody variant is labeled with an enzyme, the kit may include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

In Vivo Uses for the Antibody

It is contemplated that the antibodies of the present invention may be used to treat a mammal. In one embodiment, the antibody is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody or may be used to study toxicity of the antibody of interest. In each of these embodiments, dose escalation studies may be performed on the mammal.

The antibody or polypeptide is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody variant is suitably administered by pulse infusion, particularly with declining doses of the antibody variant. Preferably the dosing is given by injections, most preferably intravenous or subcutaneous injections, depending in part on whether the administration is brief or chronic.

For the prevention or treatment of disease, the appropriate dosage of the antibody or polypeptide will depend on the type of disease to be treated, the severity and course of the disease, whether the antibody variant is administered for preventive or therapeutic purposes, previous therapy, the patient's clinical history and response to the antibody, and the discretion of the attending physician.

Depending on the type and severity of the disease, about 0.1 mg/kg to 150 mg/kg (e.g., 0.1-20 mg/kg) of antibody is an initial candidate dosage for administration to the patient, whether, for example, by one or more separate administrations, or by continuous infusion. A typical daily dosage might range from about 1 mg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188.

The antibody compositions may be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat a disease or disorder. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as used hereinbefore or about from 1 to 99% of the heretofore employed dosages.

The antibodies of the present invention which recognize Factor D as their target may be used to treat complement-mediated disorders. These disorders are associated with excessive or uncontrolled complement activation. They include: Complement activation during cardiopulmonary bypass operations; complement activation due to ischemia-reperfusion following acute myocardial infarction, aneurysm, stroke, hemorrhagic shock, crush injury, multiple organ failure, hypobolemic shock and intestinal ischemia. These disorders can also include disease or condition is an inflammatory condition such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. It also includes autoimmune disease such as systemic lupus erythematosus, myasthenia gravis, rheumatoid arthritis, Alzheimer's disease and multiple sclerosis. Complement activation is also associated with transplant rejection. Recently there has been a strong correlation shown between complement activation and ocular diseases such as age-related macular degeneration, diabetic retinopathy.

EXAMPLES

The following examples are offered by way of illustration and not by way of limitation.

Example 1

Humanization of Factor D Murine MAb 166-32

The sequences of the heavy chain variable region ($V_H$) and the light chain variable region ($V_L$) of murine mAb 166-32 were compared with human antibody germline sequences available in the public databases. Several criteria were used when deciding on a template as described in step 1 above, including overall length, similar CDR position within the framework, overall homology, size of the CDR, etc. All of these criteria taken together provided a result for choosing the optimal human template as shown in the sequence alignment between 166-32 MAb heavy and light chain sequences and the respective human template sequences depicted in FIGS. 3 and 4.

In this case, more than one human framework template was used to design this antibody. The human template chosen for the $V_H$ chain was a combination of VI-4.1b+(7-04.1 locus) (access#X62110) (VH7 family) and JH4d (See FIG. 3). The human template chosen for the $V_L$ chain was a combination of DPK4 (VK I family) combined with JK2 (See FIG. 4).

Once the template was chosen, a Fab library was constructed by DNA synthesis and overlapping PCR. The library was composed of synthesized MAb 166-32 CDRs synthesized with the respective chosen human templates. The overlapping nucleotides encoding partial $V_H$ and $V_L$ sequences were synthesized in the range of about 63 to about 76 nucleotides with 18 to 21 nucleotide overlaps. Vectors expressing a library of humanized Fabs against Factor D antigen were constructed, and transformed into E. coli DH10B then plated on XL-1B bacterial lawn.

Library quality was evaluated for the size (the number of independent clones) and the diversity (the distribution of the mutations). The individual clones with double insertion of both light and heavy chain was about 14 out of 20 sequenced. Framework wobble mutations were evenly distributed.

PCR amplification of $V_L$ and $V_H$ gene was performed using a biotinylated forward primer containing the specific sequence to the framework region FR1 and an overhanging sequence annealed to the end of leader sequence (GeneIII) and a reverse primer from the conserved constant region (Cκ or CH1) under standard PCR conditions. The PCR product was purified by agarose gel electrophoresis, or by commercial PCR purification kit to remove unincorporated biotinylated primers and non-specific PCR.

Example 2

Library Screening

Capture Filter Lift was used for primary screening. The actual screening sized is more than 3 times larger than the theoretic library size. The candidates were further screened by single-point ELISA assay. The best binders were further confirmed by direct antigen titration using Factor D based on Fab concentration Capture Lift Screening Capture Filter Lift Assay was used for primary screening for the binding of Fab to Factor D. High titer phage were plated and incubated at 37° C. till use (about 6-8 hr). Goat anti-human kappa was diluted to 10 ug/ml in 10 ml PBST; Nitrocellulose filters for lifting plaques were prepared according to standard plaque lifting procedures and then immersed in 10 ml blocking buffer for 2 hrs on a shaker. The filters were rinsed 3× with PBST. The filters were applied to a plaque lawn and incubated at RT for approximately 15-24 hours. The filters were then removed from the plates and rinsed with TBST 3×.

Factor D (50 ug/ml) was diluted in PBST to 0.1 ug/ml and 4 ml per filter was added. The filters were incubated in the solution for 2 hr on a shaker at RT followed by rinsing 3×, each time 5 min. Diluted 166-222-HRP (1:10,000 with PBST) was added at a volume of 4 ml per filter and the filters were incubated for 1 hr on a shaker. The filters were rinsed 4×. The filters were dried and then immersed in TMB substrate followed by immersion in water to stop the reaction. Positive clones were identified.

Example 3

Single-Point ELISA Screening

Single-Point ELISA assay was used for the secondary screening. Immulon II plates were coated with goat anti-human Fab (1:12,000, 50 ul/well) over night at RT. The next day the plates were washed 4× with a plate washer. Blocking buffer was added at a volume of 100 ul per well and plates incubated for 1 hr at RT. The plates were then washed 4×.

Each Fab to be screened was added at a volume of 50 ul per well (either from 15 ml periplasmic preparation or supernatant) and incubated 1 hr at RT. Plates were washed 4× followed by the addition of 50 ul/well biotinylated factor D at 0.01 ug/ml. Plates were incubated for 1 hr at RT and then washed 4×. StreptAvidin-HRP was added (1:10,000 in PBST) and incubated for 1 hr at RT. Plates were washed 5× and then developed by adding TMB substrate at 50 ul/well. Stop buffer was added at a volume of 50 ul when it is well-developed (10-45 min) and the plates were read at 450 nm.

Example 4

Sequencing of Humanized Anti-Factor D Clones

Sixteen humanized clones with good binding affinity for human Factor D were sequenced (see Table 1). Among these, position 2 (100% human) and 49 (100% mouse) in the light chain, and position 93 (100% mouse) in the heavy chain are highly conserved indicating that they are important in maintaining antibody binding ability.

TABLE 1

Amino acid sequence analysis of humanized clones from the humanization library

| VK | 2 | 4 | 13 | 43 | 49 | 64 | 69 | VH | 2 | 9 | 38 | 93 | 97 |
|---|---|---|---|---|---|---|---|---|---|---|---|---|---|
| Mouse | T | V | M | P | S | S | A | | I | P | K | T | E |
| Human | I | M | A | V | Y | G | T | | V | S | R | V | A |
| 7 | I | M | M | V | S | S | T | | I | P | K | V | E |
| 30 | I | V | A | V | S | S | A | | V | P | K | T | E |
| 45 | I | V | M | V | S | G | A | | I | S | R | V | E |
| 46 | I | V | M | V | S | S | T | | I | S | R | V | E |
| 47 | I | V | A | V | S | S | T | | I | S | R | V | E |
| 48 | I | V | M | V | S | S | T | | V | P | R | V | E |
| 50 | I | V | M | V | S | G | A | | V | P | R | T | E |
| 51 | I | M | M | V | S | G | T | | I | S | K | T | E |
| 56 | I | V | A | V | S | G | T | | V | P | K | T | E |
| 57 | I | M | M | V | S | S | A | | V | S | R | V | E |
| 58 | I | V | M | P | S | G | A | | V | P | R | V | E |
| 59 | I | V | A | P | S | S | T | | V | P | K | V | E |
| 60 | I | V | M | P | S | G | T | | V | P | R | V | E |
| 63 | I | V | M | V | S | S | T | | V | S | R | T | E |
| 74 | I | V | M | V | S | S | T | | I | S | R | V | E |

Clone #56 was evaluated by BIAcore analysis and hemolytic inhibition assay. BIAcore analysis showed that clone #56 has a similar affinity to human Factor D as chimeric 166-32 Fab (see Table 4). Hemolytic inhibition assay showed that clone #56 is somewhat more potent than chimeric 166-32 Fab (see FIG. 6). Clone # 56 contains two murine residues in the framework of light chain and four murine residues in the heavy chain. (see Table 1). Based on these results, further optimization was carried out.

TABLE 2

Amino acid sequence analysis of optimized antibodies from the humanization/CDR3s optimization library

| VK Positions | 2 | 4 | 13 | 43 | 49 | 64 | 69 | CDR-L3 | 92 | 93 | 97 |
|---|---|---|---|---|---|---|---|---|---|---|---|
| 166-32 | T | V | M | P | S | S | A | | D | N | T |
| Human Template | I | M | A | V | Y | G | T | | | | |
| 104 | I | V | M | P | S | S | T | | D | S | T |
| 109 | I | V | A | V | S | G | A | | M | N | T |
| 111 | I | V | A | V | S | G | T | | D | S | T |
| 112 | I | V | A | V | S | G | T | | D | S | T |
| 114 | I | V | A | V | S | G | T | | D | C | T |
| 121 | I | V | A | V | S | S | A | | D | N | T |
| 125 | I | V | A | P | S | S | T | | D | N | T |
| 130 | I | V | A | V | S | S | T | | D | N | S |

| VH Positions | 2 | 9 | 38 | 93 | 97 | CDR-H3 | 98 | 99 | 100 |
|---|---|---|---|---|---|---|---|---|---|
| 166-32 | I | P | K | T | E | | V | D | N |
| Human Template | V | S | R | V | A | | | | |
| 104 | V | S | R | V | E | | V | D | T |
| 109 | V | S | R | V | E | | V | N | N |
| 111 | V | S | R | V | E | | V | N | N |
| 112 | V | S | R | V | E | | V | N | N |
| 114 | V | S | K | V | E | | V | N | N |
| 121 | I | S | R | V | E | | V | N | T |
| 125 | V | S | R | V | E | | P | D | N |
| 130 | V | S | R | V | E | | V | D | H |

Figure 7:
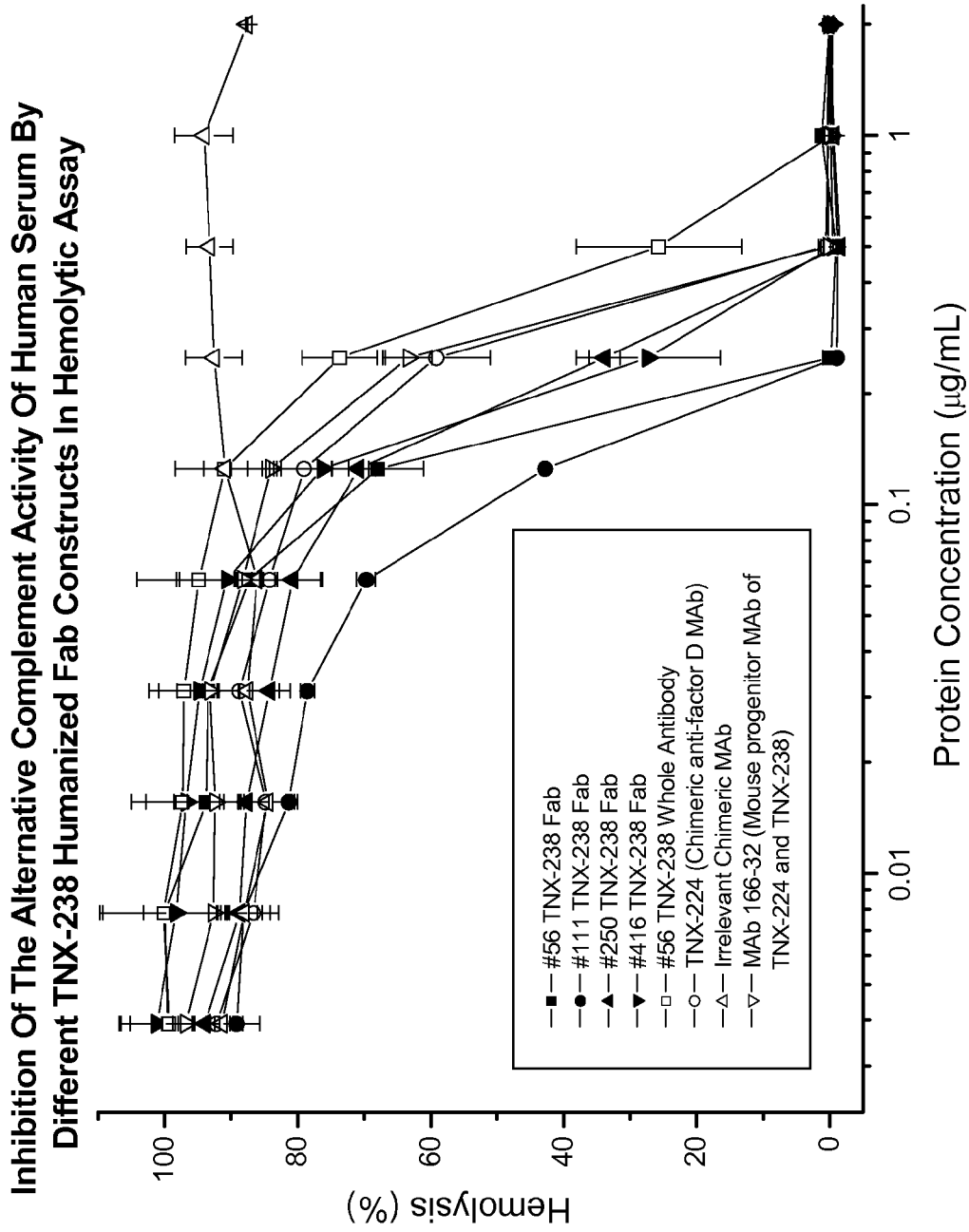
FIG. 7 depicts the inhibition of the alternative complement activity by humanized antibody Fab clones #56, #111, #250, and #416.

Clone #111 and #114 were characterized by BIAcore analysis (see Table 4). Clone #104, #111, #114 and #130 were also characterized by hemolytic inhibition assay (see FIG. 6). These clones have higher affinities than chimeric 166-32, and are more potent than chimeric Fab in inhibiting the alternative pathway as shown by hemolytic inhibition assay (FIG. 7). Clone #111 contains the same two murine residues in the light chain (position 4 and 49) as clone #56. It also contains the conserved murine residue in the heavy chain position 97 as found in clone #56. There is one beneficial mutation in both light and heavy chain CDR3 in clone #111. From two independent libraries screened (humanization library, and humanization/CDR3s optimization library), we found that the best clones have similar consensus residues.

To further optimize the affinity of clone #111, an antibody library was constructed by introducing single mutations into the CDR-H1 and CDR-L2 simultaneously. In brief, site-directed mutagenesis approach was used to construct such libraries by annealing oligonucleotides encoding single mutations to the template of clone #111. A total of 24 clones with very high affinity to human Factor D were sequenced. Among those 24 clones, several redundant beneficial mutations were identified. Clones #250, #315, #345 and #416 were selected for BIAcore analysis (see Table 4). BIAcore data showed that these clones have higher affinity to human Factor D than initial clone #111. Clone #250, #315, #348 and #416 were also tested in the hemolytic inhibition assay (see FIG. 6) and inhibition of the alternative pathway (FIG. 7).

Example 5

AP Hemolysis Assay

Biological function of the humanized clones was determined using hemolytic inhibition assay and BIAcore analysis (See Example 6 below). Hemolytic assay was performed according to the following procedure. 20 ul of 1:20 diluted rabbit red blood cells (RRBC) (0.5 ml+9.5 ml GVB/Mg- EGTA buffer) in 20 ml Saline (0.9% NaCl) at approximately 1:2×10⁴ dilution were counted by Coulter Counter. The cell concentration was then adjusted to about 2-5×10⁴ cells/ml. Each plate received about 500×10⁶/plate RRBC or about 1 ml RRBC/plate (500×10⁶/2-5×10⁴).

Cells were diluted in 6 ml GVB/Mg-EGTA buffer/plate, mixed and washed 3 times by spinning at 1360 rpm×4 min at 4° C. The RRBC pellet is suspended in 3 ml GVB/Mg-EGTA buffer/plate and kept on ice.

Human serum from −80° C. freezer was thawed just prior to use. The serum was diluted to a concentration of 20% serum in GVB/Mg-EGTA buffer, 5 ml/plate (final is 10%) and kept on ice.

TABLE 3

|  | 1 | 2 | 3 | S | SB |
|---|---|---|---|---|---|
| GVB/Mg-EGTA: | 50 ul | 50 ul | 50 ul | 50 ul | 50 ul |
| mAb: 50 ul mix | 50 ul | 50 ul | 50 ul | — | — |
| 20% Hu serum: | 50 ul | 50 ul | 50 ul | 50 ul | 50 ul |
| Shake 30 sec at 5-6°, then keep at RT for 7 min. | | | | | |
| Rabbit RBC: | 30 ul | 30 ul | 30 ul |  | 30 ul |

Samples were shaken for 30 sec at 5-6° C. and then for 40 minutes at 37° C. Samples were cooled to 5-6° C. while shaking and then centrifuged at 2,000 rpm×3 min at 4° C. Approximately 80 ul supernatant was transferred to a flat-bottom 96 well plate and the OD value at 590 nm was read using a standard plate reader. The percent inhibition was calculated as follows: % Inhibition={[(S-SB)−(U-SB)]/(S-SB)}×100%. (U=sample 1, 2 or 3 (columns 1, 2 or 3 of Table 3, respectively).

Example 6

Kinetic Analysis of Anti-Human Factor D Fab by BiaCore

Immobilization—Human factor D (Advanced Research Inc, 0.1 mg/ml) was directly immobilized onto the CM5 chip (BiaCore) using amine-coupling method. The procedure is briefly described as following: (1) Constant flow (PBS) is at 5 μl/min. (2) Injection of 35 μl EDC/NHS (1:1). (3) Injection of 35 μl of human factor D in acetate buffer, pH 4.5. (4) Block the activated group by injection of 35 μl etholamine. (5) Clean-up the surface by 5 μl 10 mM Glycine pH 1.5. The ligand (human factor D) immobilization level is about 1,000 RU. Test run using α-human factor D (huDi, 40 μl, 31.5 μg/ml) yielded a relative response around 900 RU.

Kinetic analysis—All anti-human factor D Fabs were diluted in PBS buffer. Each sample was prepared in a series of concentrations: 12.5 nM, 25 nM, 50 nM, 75 nM, 100 nM, 125 nM, and 150 nM, with 40 μl injection pulse at high acquisition rate. Regeneration was accomplished by applying 5 μl pulse of 10 mM Glycine at pH 1.5. Kinetic parameters were obtained by fitting Fabs binding traces to 1:1 binding model under pseudo-first order kinetic using BIAvaluation version 3.0. The results are presented in Table 4 below. All data are obtained by global fitting routine.

TABLE 4

BIAcore Results

| Fab Clone | ka (M − 1 s − 1) | kd (s − 1) | Kd (M) |
|---|---|---|---|
| Anti-factor D Fab 315 | $7.1 \times 10^5$ | $2.7 \times 10^{-4}$ | $3.7 \times 10^{-10}$ |
| Anti-factor D Fab 416 | $8.2 \times 10^5$ | $1.8 \times 10^{-4}$ | $3.3 \times 10^{-10}$ |
| Anti-factor D Fab 345 | $6.8 \times 10^5$ | $3.5 \times 10^{-4}$ | $5.1 \times 10^{-10}$ |
| Anti-factor D Fab 250 | $5.7 \times 10^5$ | $1.9 \times 10^{-4}$ | $3.3 \times 10^{-10}$ |
| Anti-factor D Fab 56 | $3.6 \times 10^5$ | $9.8 \times 10^{-4}$ | $2.7 \times 10^{-9}$ |
| chimeric | $4.4 \times 10^5$ | $1.2 \times 10^{-3}$ | $2.7 \times 10^{-9}$ |
| Anti-factor D Fab 111 | $3.3 \times 10^5$ | $3.7 \times 10^{-4}$ | $1.14 \times 10^{-9}$ |

Those skilled in the art will recognize, or be able to ascertain using no more than routine experimentation, many equivalents to the specific embodiments of the invention described herein. Such equivalents are intended to be encompassed by the following claims.

We claim:

1. A variable domain of a humanized anti-Factor D antibody comprising a heavy chain variable domain amino acid sequence selected from the group consisting of: SEQ ID NO: 6; SEQ ID NO: 8; SEQ ID NO: 10; and SEQ ID NO: 12.

2. A variable domain of a humanized anti-Factor D antibody comprising a light chain variable domain amino acid sequence selected from the group consisting of SEQ ID NO: 5; SEQ ID NO: 7; SEQ ID NO: 9 and SEQ ID NO: 11.

3. A humanized anti-Factor D antibody comprising the light chain variable domain sequence of SEQ ID NO: 5 and the heavy chain variable domain sequence of SEQ ID NO: 6.

4. A humanized anti-Factor D antibody comprising the light chain variable domain sequence of SEQ ID NO: 7 and the heavy chain variable domain sequence of SEQ ID NO: 8.

5. A humanized anti-Factor D antibody comprising the light chain variable domain sequence of SEQ ID NO: 9 and the heavy chain variable domain sequence of SEQ ID NO: 10.

6. A humanized anti-Factor D antibody comprising the light chain variable domain sequence of SEQ ID NO: 11 and the heavy chain variable domain sequence of SEQ ID NO: 12.

7. A humanized anti-Factor D antibody having a variable light chain comprising a CDR-L1 having the sequence of SEQ ID NO: 16; a CDR-L2 having the sequence of SEQ ID NO: 21, or 24; and a CDR-L3 having the sequence of SEQ ID NO: 18, 19 or 22; and a variable heavy chain comprising a CDR-H1 having the sequence of SEQ ID NO: 13, 23 or 25; a CDR-H2 having the sequence of SEQ ID NO: 14; and a CDR-H-3 having the sequence of SEQ ID NO: 15 or 20.

8. A humanized anti-Factor D antibody having a variable light chain comprising a CDR-L1 having the sequence of SEQ ID NO: 16; a CDR-L2 having the sequence of SEQ ID NO: 17, 21 or 24, and a CDR-L3 having the sequence of SEQ ID NO: 19 or 22, and a variable heavy chain comprising a CDR-H1 having the sequence of SEQ ID NO: 13, 23 or 25; a CDR-H2 having the sequence of SEQ ID NO: 14; and a CDR-H3 having the sequence of SEQ ID NO: 15 or 20.

9. A polypeptide comprising the following amino acid sequence:

QX$_1$QLVQSGX$_2$E LKKPGASVKV SCKASGYTFT SYGMNWVX$_3$QA PGQGLEWMGW INTYTGET-TYADDFKGRFVF SLDTSVSTAY LQISSLKAED TAX$_4$YYCX$_5$REG GVNNWGQGTL VTVSS (SEQ ID NO: 27), wherein X$_1$ is I or V; X$_2$ is P or S; X$_3$ is K or R; X$_4$ is T or V; and X$_5$ is E or A.

10. A polypeptide comprising the following amino acid sequence:

DIQX$_6$TQSPSSLSX$_7$SVGDRVTITCITSTDIDDDMNW-YQQKPGKX$_8$PKLLIX$_9$DGNTLRPGV PSRFSX$_{10}$S-GSGX$_{11}$DFTLTISSLQPEDVATYYCLQSDSLPYTF-GQ GTKLEIK (SEQ ID NO: 26), wherein X$_6$ is V or M; X$_7$ is M or A; X$_8$ is P or V; X$_9$ is S or Y; X$_{10}$ is S or G and X$_{11}$ is A or T.

11. A polypeptide comprising the amino acid sequence of SEQ ID NO: 6, 8, 10, or 12.

12. A polypeptide comprising the amino acid sequence of SEQ ID NO: 5, 7, 9, or 11.

13. A humanized anti-Factor D antibody comprising a polypeptide having the amino acid sequence of SEQ ID NO: 27, wherein $X_1$ is I or V; $X_2$ is P or S; $X_3$ is K or R; $X_4$ is T or V; and $X_5$ is E or A.

14. A humanized anti-Factor D antibody comprising a polypeptide having the amino acid sequence of SEQ ID NO: 26, wherein $X_6$ is V or M; $X_7$ is M or A; $X_8$ is P or V; $X_9$ is S or Y; $X_{10}$ is S or G and $X_{11}$ is A or T; or a polypeptide having the amino acid sequence of SEQ ID NO: 26, wherein $X_6$ is V or M; $X_7$ is M or A; $X_8$ is P or V; $X_9$ is S or Y; $X_{10}$ is S or G and $X_{11}$ is A or T, and wherein the amino acid at position 104 of SEQ ID NO:26 is a valine or a leucine.

15. A humanized anti-Factor D antibody comprising
   (i) a polypeptide having the amino acid sequence of SEQ ID NO: 27, wherein $X_1$ is I or V; $X_2$ is P or S; $X_3$ is K or R; $X_4$ is T or V; and $X_5$ is E or A; and
   (ii) a polypeptide having the amino acid sequence of SEQ ID NO: 26, wherein $X_6$ is V or M; $X_7$ is M or A; $X_8$ is P or V; $X_9$ is S or Y; $X_{10}$ is S or G and $X_{11}$ is A or T; or a polypeptide having the amino acid sequence of SEQ ID NO: 26, wherein $X_6$ is V or M; $X_7$ is M or A; $X_8$ is P or V; $X_9$ is S or Y; $X_{10}$ is S or G and $X_{11}$ is A or T, and wherein the amino acid at position 104 of SEQ ID NO:26 is a valine or a leucine.

16. The variable domain of claim 2 wherein amino acid at position 104 of SEQ ID NO: 7 is a valine or a leucine.

17. The humanized anti-Factor D antibody of claim 4 comprising the variable domain sequence of SEQ ID NO: 7 wherein the amino acid at position 104 of SEQ ID NO: 7 is a valine or a leucine and the variable domain sequence of SEQ ID NO: 8.

18. The polypeptide of claim 10 wherein the amino acid at position 104 of SEQ ID NO: 26 is a valine or a leucine.

19. The polypeptide of claim 12 wherein the amino acid at position 104 of SEQ ID NO: 7 is a valine or a leucine.

20. A humanized anti-Factor D antibody comprising a heavy chain variable domain amino acid sequence selected from the group consisting of: SEQ ID NO: 6; SEQ ID NO: 8; SEQ ID NO: 10; and SEQ ID NO: 12.

21. A humanized anti-Factor D antibody comprising a light chain variable domain amino acid sequence selected from the group consisting of SEQ ID NO: 5; SEQ ID NO: 7; SEQ ID NO: 9 and SEQ ID NO: 11.

22. A humanized anti-Factor D antibody having a variable light chain comprising a CDR-L1 having the sequence of SEQ ID NO: 16; a CDR-L2 having the sequence of SEQ ID NO: 17, 21 or 24; and a CDR-L3 having the sequence of SEQ ID NO: 18, 19 or 22; and a variable heavy chain comprising a CDR-H1 having the sequence of SEQ ID NO: 23 or 25; a CDR-H2 having the sequence of SEQ ID NO: 14; and a CDR-H3 having the sequence of SEQ ID NO: 15 or 20.

23. A humanized anti-Factor D antibody having a variable light chain comprising a CDR-L1 having the sequence of SEQ ID NO: 16; a CDR-L2 having the sequence of SEQ ID NO: 17, 21 or 24; and a CDR-L3 having the sequence of SEQ ID NO: 18, 19 or 22; and a variable heavy chain comprising a CDR-H1 having the sequence of SEQ ID NO: 13, 23 or 25; a CDR-H2 having the sequence of SEQ ID NO: 14; and a CDR-H3 having the sequence of SEQ ID NO: 20.

24. An anti-Factor D antibody fragment of the antibody of any one of claims 3-8, 13-14, 17, 20-23, 15.

25. A composition comprising the variable domain of any one of claim 1, 2 or 16.

26. A composition comprising the polypeptide of any one of claim 9-12, 18 or 19.

27. A composition comprising the anti-Factor D antibody fragment of claim 24.

28. A composition comprising the antibody of any one of claims 3-8, 13, 14, 17, 20, 24.

* * * * *

UNITED STATES PATENT AND TRADEMARK OFFICE
CERTIFICATE OF CORRECTION

| | | |
|---|---|---|
| PATENT NO. | : 8,067,002 B2 | Page 1 of 1 |
| APPLICATION NO. | : 11/931060 | |
| DATED | : November 29, 2011 | |
| INVENTOR(S) | : Ling-Ling An et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 689 days.

Signed and Sealed this

Thirteenth Day of March, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,067,002 B2 | |
| APPLICATION NO. | : 11/931060 | |
| DATED | : November 29, 2011 | |
| INVENTOR(S) | : Ling-Ling An et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 688 days.

Signed and Sealed this
Tenth Day of April, 2012

David J. Kappos
*Director of the United States Patent and Trademark Office*

UNITED STATES PATENT AND TRADEMARK OFFICE
CERTIFICATE OF CORRECTION

PATENT NO. : 8,067,002 B2
APPLICATION NO. : 11/931060
DATED : November 29, 2011
INVENTOR(S) : An et al.

Page 1 of 1

It is certified that error appears in the above-identified patent and that said Letters Patent is hereby corrected as shown below:

In claim 28, column 68, lines 33-34, please replace "the antibody of any one of claims 3-8, 13, 14, 17, 20, 24" with "the antibody of any one of claims 3-8, 13-15, 17, and 20-23".

Signed and Sealed this
Twenty-second Day of January, 2013

David J. Kappos
*Director of the United States Patent and Trademark Office*

SEQUENCE LISTING

<160> NUMBER OF SEQ ID NOS: 58

<210> SEQ ID NO 1
<211> LENGTH: 115
<212> TYPE: PRT
<213> ORGANISM: ARTIFICIAL
<220> FEATURE:
<223> OTHER INFORMATION: VARIABLE HEAVY CHAIN DOMAIN OF MAB 166-32

<400> SEQUENCE: 1

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Thr Tyr Ala Asp Asp Phe
    50                  55                  60

Lys Gly Arg Phe Val Phe Ser Leu Glu Thr Ser Ala Ser Thr Ala Tyr
65                  70                  75                  80

Leu Glu Ile Asn Asn Leu Lys Asn Glu Asp Met Ala Thr Tyr Phe Cys
                    85                  90                  95

Glu Arg Glu Gly Gly Val Asp Asn Trp Gly Gln Gly Thr Thr Leu Thr
                100                 105                 110

Val Ser Ser
        115

<210> SEQ ID NO 2
<211> LENGTH: 107
<212> TYPE: PRT
<213> ORGANISM: ARTIFICIAL
<220> FEATURE:
<223> OTHER INFORMATION: VARIABLE LIGHT CHAIN DOMAIN OF MAB 166-32

<400> SEQUENCE: 2

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
                20                  25                  30

Met Asn Trp Tyr Gln Gln Lys Pro Gly Glu Pro Pro Lys Leu Leu Ile
            35                  40                  45

Ser Gly Gly Asn Thr Leu Arg Pro Gly Val Pro Ser Arg Phe Ser Ser
        50                  55                  60

Ser Gly Tyr Gly Ala Asp Phe Val Phe Thr Ile Asp Asn Met Leu Ser
65                  70                  75                  80

Glu Asp Val Ala Asp Tyr Tyr Cys Leu Gln Ser Asp Asn Leu Pro Tyr
                85                  90                  95

Thr Phe Gly Gly Gly Thr Arg Leu Glu Ile Lys
            100                 105

<210> SEQ ID NO 3
<211> LENGTH: 345
<212> TYPE: DNA
<213> ORGANISM: ARTIFICIAL
<220> FEATURE:
<223> OTHER INFORMATION: VARIABLE HEAVY CHAIN DOMAIN OF MAB 166-32

<400> SEQUENCE: 3
cagatccagt tggtgcagtc tggacctgag ctgaagaagc ctggagagac agtcaagatc      60
tcctgcaagg cttctgggta taccttcaca aactatggaa tgaactgggt gaagcaggct     120
ccaggaaagg gtttaaagtg gatgggctgg ataaacacct acactggaga gacaacatat     180
gctgatgact caagggacg gtttgtcttc tctttggaaa cctctgccag cactgcctat     240
ttggagatca caaccctcaa aaatgaggac atggctacat atttctgtga aagagagggg     300
ggggttgaca ctggggcca aggcaccact ctcacagtct cctca                       345

<210> SEQ ID NO 4
<211> LENGTH: 321
<212> TYPE: DNA
<213> ORGANISM: ARTIFICIAL
<220> FEATURE:
<223> OTHER INFORMATION: VARIABLE LIGHT CHAIN DOMAIN OF MAB 166-32

<400> SEQUENCE: 4
gaaacaactg tgacccagtc tcctgcatcc ctgtccatgg ctataggaga aaaagtcacc      60
atcagatgca taaccagcac tgatattgat gatgatatga actggtacca gcagaagcca     120
ggggaacctc ctaagctcct tatttcagga ggcaatactc ttcgtcctgg agtcccatcc     180
cgattctcca gcagtggcta tggtgcagat tttgttttta caattgacaa catgctctca     240

```
gaagatgttg cagattacta ctgtttgcaa agtgataact tgccgtacac gttcggaggg    300
gggaccaggc tggaaataaa a                                              321
```

<210> SEQ ID NO 5
<211> LENGTH: 107
<212> TYPE: PRT
<213> ORGANISM: ARTIFICIAL
<220> FEATURE:
<223> OTHER INFORMATION: VARIABLE LIGHT CHAIN DOMAIN OF HUMANIZED CLONE
      #56

<400> SEQUENCE: 5

Asp Ile Gln Val Thr Gln Ser Pro Ser Ser Leu Ser Ala Ser Val Arg
1               5                   10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Asn Leu Pro Tyr
                85                  90                  95

Thr Phe Gly Gln Gly Thr Lys Leu Glu Ile Lys
            100                 105

<210> SEQ ID NO 6
<211> LENGTH: 115
<212> TYPE: PRT
<213> ORGANISM: ARTIFICIAL
<220> FEATURE:
<223> OTHER INFORMATION: VARIABLE HEAVY CHAIN DOMAIN OF HUMANIZED CLONE
      #56

<400> SEQUENCE: 6

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Thr Tyr Tyr Cys
                85                  90                  95

Glu Arg Glu Gly Gly Val Asp Asn Trp Gly Gln Gly Thr Leu Val Thr
            100                 105                 110

Val Ser Ser
        115

<210> SEQ ID NO 7
<211> LENGTH: 107
<212> TYPE: PRT
<213> ORGANISM: ARTIFICIAL
<220> FEATURE:
<223> OTHER INFORMATION: VARIABLE LIGHT CHAIN DOMAIN OF HUMANIZED CLONE
      #111

<400> SEQUENCE: 7

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Leu Glu Ile Lys
            100                 105

<210> SEQ ID NO 8
<211> LENGTH: 115
<212> TYPE: PRT
<213> ORGANISM: ARTIFICIAL
<220> FEATURE:
<223> OTHER INFORMATION: VARIABLE HEAVY CHAIN DOMAIN OF HUMANIZED CLONE
      #111

<400> SEQUENCE: 8

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser
        115

<210> SEQ ID NO 9
<211> LENGTH: 107
<212> TYPE: PRT
<213> ORGANISM: ARTIFICIAL
<220> FEATURE:
<223> OTHER INFORMATION: VARIABLE LIGHT CHAIN DOMAIN OF HUMANIZED CLONE
      #250

<400> SEQUENCE: 9

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Val Pro Lys Leu Leu Ile
        35                  40                  45

Ser His Gly Asn Thr Leu Arg Pro Gly Val Pro Ser Arg Phe Ser Gly

```
                    50                  55                  60
Ser Gly Ser Gly Thr Asp Phe Thr Leu Thr Ile Ser Ser Leu Gln Pro
 65                  70                  75                  80

Glu Asp Val Ala Thr Tyr Tyr Cys Leu Gln Ser Asp Ser Leu Pro Tyr
                 85                  90                  95

Thr Phe Gly Gln Gly Thr Lys Leu Glu Ile Lys
                100                 105

<210> SEQ ID NO 10
<211> LENGTH: 115
<212> TYPE: PRT
<213> ORGANISM: ARTIFICIAL
<220> FEATURE:
<223> OTHER INFORMATION: VARIABLE HEAVY CHAIN DOMAIN OF HUMANIZED CLONE
      #250

<400> SEQUENCE: 10

Gln Val Gln Leu Val Gln Ser Gly Pro Glu Leu Lys Lys Pro Gly Ala
  1               5                  10                  15

Ser Val Lys Val Ser Cys Lys Ala Ser Gly Tyr Thr Phe Thr Asn Tyr
                 20                  25                  30

Gly Leu Asn Trp Val Arg Gln Ala Pro Gly Gln Gly Leu Glu Trp Met
             35                  40                  45

Gly Trp Ile Asn Thr Tyr Thr Gly Glu Thr Thr Tyr Ala Asp Asp Phe
         50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Glu Arg Glu Gly Gly Val Asn Asn Trp Gly Gln Gly Thr Leu Val Thr
                100                 105                 110

Val Ser Ser
        115

<210> SEQ ID NO 11
<211> LENGTH: 107
<212> TYPE: PRT
<213> ORGANISM: ARTIFICIAL
<220> FEATURE:
<223> OTHER INFORMATION: VARIABLE LIGHT CHAIN DOMAIN OF HUMANIZED CLONE
      #416

<400> SEQUENCE: 11

Asp Ile Gln Val Thr Gln Ser Pro Ser Ser Leu Ser Ala Ser Val Gly
  1               5                  10                  15

Asp Arg Val Thr Ile Thr Cys Ile Thr Ser Thr Asp Ile Asp Asp Asp
                 20                  25                  30

Met Asn Trp Tyr Gln Gln Lys Pro Gly Lys Val Pro Lys Leu Leu Ile
             35                  40                  45

Ser Asp Gly Asn Thr Leu Arg Pro Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Leu Gln Ser Asp Ser Leu Pro Tyr
                 85                  90                  95

Thr Phe Gly Gln Gly Thr Lys Leu Glu Ile Lys
                100                 105

<210> SEQ ID NO 12
```

```
<211> LENGTH: 115
<212> TYPE: PRT
<213> ORGANISM: ARTIFICIAL
<220> FEATURE:
<223> OTHER INFORMATION: VARIABLE HEAVY CHAIN DOMAIN OF HUMANIZED CLONE
      #416

<400> SEQUENCE: 12

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser
        115

<210> SEQ ID NO 13
<211> LENGTH: 10
<212> TYPE: PRT
<213> ORGANISM: ARTIFICIAL
<220> FEATURE:
<223> OTHER INFORMATION: CDR-H1 OF MAB 166-32

<400> SEQUENCE: 13

Gly Tyr Thr Phe Thr Asn Tyr Gly Met Asn
1               5                   10

<210> SEQ ID NO 14
<211> LENGTH: 19
<212> TYPE: PRT
<213> ORGANISM: ARTIFICIAL
<220> FEATURE:
<223> OTHER INFORMATION: CDR-H2 OF MAB 166-32

<400> SEQUENCE: 14

Trp Met Gly Trp Ile Asn Thr Tyr Thr Gly Glu Thr Thr Tyr Ala Asp
1               5                   10                  15

Asp Phe Lys

<210> SEQ ID NO 15
<211> LENGTH: 6
<212> TYPE: PRT
<213> ORGANISM: ARTIFICIAL
<220> FEATURE:
<223> OTHER INFORMATION: CDR-H3 OF MAB 166-32

<400> SEQUENCE: 15

Glu Gly Gly Val Asp Asn
1               5

<210> SEQ ID NO 16
<211> LENGTH: 11
<212> TYPE: PRT
<213> ORGANISM: ARTIFICIAL
<220> FEATURE:
```

<223> OTHER INFORMATION: CDR-L1 OF MAB 166-32

<400> SEQUENCE: 16

Ile Thr Ser Thr Asp Ile Asp Asp Met Asn
1               5                   10

<210> SEQ ID NO 17
<211> LENGTH: 7
<212> TYPE: PRT
<213> ORGANISM: ARTIFICIAL
<220> FEATURE:
<223> OTHER INFORMATION: CDR-L2 OF MAB 166-32

<400> SEQUENCE: 17

Gly Gly Asn Thr Leu Arg Pro
1               5

<210> SEQ ID NO 18
<211> LENGTH: 9
<212> TYPE: PRT
<213> ORGANISM: ARTIFICIAL
<220> FEATURE:
<223> OTHER INFORMATION: CDR-L3 OF MAB 166-32

<400> SEQUENCE: 18

Leu Gln Ser Asp Asn Leu Pro Tyr Thr
1               5

<210> SEQ ID NO 19
<211> LENGTH: 9
<212> TYPE: PRT
<213> ORGANISM: ARTIFICIAL
<220> FEATURE:
<223> OTHER INFORMATION: CDR-L3 OF HUMANIZED CLONE #111

<400> SEQUENCE: 19

Leu Gln Ser Asp Ser Leu Pro Tyr Thr
1               5

<210> SEQ ID NO 20
<211> LENGTH: 6
<212> TYPE: PRT
<213> ORGANISM: ARTIFICIAL
<220> FEATURE:
<223> OTHER INFORMATION: CDR-H3 OF HUMANIZED CLONE #111

<400> SEQUENCE: 20

Glu Gly Gly Val Asn Asn
1               5

<210> SEQ ID NO 21
<211> LENGTH: 7
<212> TYPE: PRT
<213> ORGANISM: ARTIFICIAL
<220> FEATURE:
<223> OTHER INFORMATION: CDR-L2 OF HUMANIZED CLONE #250

<400> SEQUENCE: 21

His Gly Asn Thr Leu Arg Pro
1               5

<210> SEQ ID NO 22
<211> LENGTH: 9
<212> TYPE: PRT
<213> ORGANISM: ARTIFICIAL
<220> FEATURE:
<223> OTHER INFORMATION: CDR-L3 OF HUMANIZED CLONE #250

```
<400> SEQUENCE: 22

Leu Gln Ser Asp Ser Leu Pro Tyr Thr
1               5

<210> SEQ ID NO 23
<211> LENGTH: 10
<212> TYPE: PRT
<213> ORGANISM: ARTIFICIAL
<220> FEATURE:
<223> OTHER INFORMATION: CDR-H1 OF HUMANIZED CLONE #250

<400> SEQUENCE: 23

Gly Tyr Thr Phe Thr Asn Tyr Gly Leu Asn
1               5                   10

<210> SEQ ID NO 24
<211> LENGTH: 7
<212> TYPE: PRT
<213> ORGANISM: ARTIFICIAL
<220> FEATURE:
<223> OTHER INFORMATION: CDR-L2 OF HUMANIZED CLONE #416

<400> SEQUENCE: 24

Asp Gly Asn Thr Leu Arg Pro
1               5

<210> SEQ ID NO 25
<211> LENGTH: 10
<212> TYPE: PRT
<213> ORGANISM: ARTIFICIAL
<220> FEATURE:
<223> OTHER INFORMATION: CDR-H1 OF HUMANIZED CLONE #416

<400> SEQUENCE: 25

Gly Tyr Thr Phe Thr Ser Tyr Gly Met Asn
1               5                   10

<210> SEQ ID NO 26
<211> LENGTH: 107
<212> TYPE: PRT
<213> ORGANISM: ARTIFICIAL
<220> FEATURE:
<223> OTHER INFORMATION: VARIABLE LIGHT CHAIN COMPOSITE OF HUMANIZED
      CLONES
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid

<400> SEQUENCE: 26

Asp Ile Gln Xaa Thr Gln Ser Pro Ser Ser Leu Ser Xaa Ser Val Gly
```

```
                    1               5                   10                  15
Asp Arg Val Thr Ile Thr Cys Ile Thr Ser Thr Asp Ile Asp Asp
                20                  25                  30

Met Asn Trp Tyr Gln Gln Lys Pro Gly Lys Xaa Pro Lys Leu Leu Ile
                35                  40                  45

Xaa Asp Gly Asn Thr Leu Arg Pro Gly Val Pro Ser Arg Phe Ser Xaa
                50                  55                  60

Ser Gly Ser Gly Xaa Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Leu Glu Ile Lys
                100                 105

<210> SEQ ID NO 27
<211> LENGTH: 115
<212> TYPE: PRT
<213> ORGANISM: ARTIFICIAL
<220> FEATURE:
<223> OTHER INFORMATION: VARIABLE HEAVY CHAIN COMPOSITE OF HUMANIZED
      CLONES
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid

<400> SEQUENCE: 27

Gln Xaa Gln Leu Val Gln Ser Gly Xaa Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Gly Met Asn Trp Val Xaa Gln Ala Pro Gly Gln Gly Leu Glu Trp Met
                35                  40                  45

Gly Trp Ile Asn Thr Tyr Thr Gly Glu Thr Thr Tyr Ala Asp Asp Phe
                50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Xaa Tyr Tyr Cys
                85                  90                  95

Xaa Arg Glu Gly Gly Val Asn Asn Trp Gly Gln Gly Thr Leu Val Thr
                100                 105                 110

Val Ser Ser
        115

<210> SEQ ID NO 28
<211> LENGTH: 87
<212> TYPE: PRT
<213> ORGANISM: ARTIFICIAL
```

<220> FEATURE:
<223> OTHER INFORMATION: Sequence is synthesized

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Trp Val
            20                  25                  30

Arg Gln Ala Pro Gly Gln Gly Leu Glu Trp Met Gly Arg Val Thr Ile
        35                  40                  45

Thr Ala Asp Thr Ser Thr Ser Thr Ala Tyr Met Glu Leu Ser Ser Leu
    50                  55                  60

Arg Ser Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 29
<211> LENGTH: 81
<212> TYPE: PRT
<213> ORGANISM: ARTIFICIAL
<220> FEATURE:
<223> OTHER INFORMATION: Sequence is synthesized

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Trp Val Arg Gln Ala Pro Gly
            20                  25                  30

Gln Gly Leu Glu Trp Met Arg Val Thr Ile Thr Ala Asp Thr Ser Thr
        35                  40                  45

Ser Thr Ala Tyr Met Glu Leu Ser Ser Leu Arg Ser Glu Asp Thr Ala
    50                  55                  60

Val Tyr Tyr Cys Ala Arg Trp Gly Gln Gly Thr Leu Val Thr Val Ser
65                  70                  75                  80

Ser

<210> SEQ ID NO 30
<211> LENGTH: 80
<212> TYPE: PRT
<213> ORGANISM: ARTIFICIAL
<220> FEATURE:
<223> OTHER INFORMATION: Sequence is synthesized

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Trp Val Arg Gln Ala Pro Gly
            20                  25                  30

Gln Gly Leu Glu Trp Met Arg Val Thr Ile Thr Ala Asp Thr Ser Thr
        35                  40                  45

Ser Thr Ala Tyr Met Glu Leu Ser Ser Leu Arg Ser Glu Asp Thr Ala
    50                  55                  60

Val Tyr Tyr Cys Ala Trp Gly Gln Gly Thr Leu Val Thr Val Ser Ser
65                  70                  75                  80

<210> SEQ ID NO 31
<211> LENGTH: 79
<212> TYPE: PRT
<213> ORGANISM: ARTIFICIAL

```
<220> FEATURE:
<223> OTHER INFORMATION: Sequence is synthesized

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Trp Val Arg Gln Ala Pro Gly
            20                  25                  30

Gln Gly Leu Glu Trp Met Arg Val Thr Ile Thr Ala Asp Thr Ser Thr
        35                  40                  45

Ser Thr Ala Tyr Met Glu Leu Ser Ser Leu Arg Ser Glu Asp Thr Ala
    50                  55                  60

Val Tyr Tyr Cys Trp Gly Gln Gly Thr Leu Val Thr Val Ser Ser
65                  70                  75

<210> SEQ ID NO 32
<211> LENGTH: 87
<212> TYPE: PRT
<213> ORGANISM: ARTIFICIAL
<220> FEATURE:
<223> OTHER INFORMATION: Sequence is synthesized

<400> SEQUENCE: 32

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Val Ser Trp Ile
            20                  25                  30

Arg Gln Pro Pro Gly Lys Gly Leu Glu Trp Ile Gly Arg Val Thr Ile
        35                  40                  45

Ser Val Asp Thr Ser Lys Asn Gln Phe Ser Leu Lys Leu Ser Ser Val
    50                  55                  60

Thr Ala Ala Asp Thr Ala Val Tyr Tyr Cys Ala Arg Trp Gly Gln Gly
65                  70                  75                  80

Thr Leu Val Thr Val Ser Ser
                85

<210> SEQ ID NO 33
<211> LENGTH: 81
<212> TYPE: PRT
<213> ORGANISM: ARTIFICIAL
<220> FEATURE:
<223> OTHER INFORMATION: Sequence is synthesized

<400> SEQUENCE: 33

Gln Val Gln Leu Gln Glu Ser Gly Pro Gly Leu Val Lys Pro Ser Gln
1               5                   10                  15

Thr Leu Ser Leu Thr Cys Thr Val Ser Trp Ile Arg Gln Pro Pro Gly
            20                  25                  30

Lys Gly Leu Glu Trp Ile Arg Val Thr Ile Ser Val Asp Thr Ser Lys
        35                  40                  45

Asn Gln Phe Ser Leu Lys Leu Ser Ser Val Thr Ala Ala Asp Thr Ala
    50                  55                  60

Val Tyr Tyr Cys Ala Arg Trp Gly Gln Gly Thr Leu Val Thr Val Ser
65                  70                  75                  80

Ser

<210> SEQ ID NO 34
<211> LENGTH: 80
<212> TYPE: PRT
<213> ORGANISM: ARTIFICIAL
```

```
<220> FEATURE:
<223> OTHER INFORMATION: Sequence is synthesized

<400> SEQUENCE: 34

Gln Val Gln Leu Gln Glu Ser Gly Pro Gly Leu Val Lys Pro Ser Gln
1               5                   10                  15

Thr Leu Ser Leu Thr Cys Thr Val Ser Trp Ile Arg Gln Pro Pro Gly
            20                  25                  30

Lys Gly Leu Glu Trp Ile Arg Val Thr Ile Ser Val Asp Thr Ser Lys
        35                  40                  45

Asn Gln Phe Ser Leu Lys Leu Ser Ser Val Thr Ala Ala Asp Thr Ala
    50                  55                  60

Val Tyr Tyr Cys Ala Trp Gly Gln Gly Thr Leu Val Thr Val Ser Ser
65                  70                  75                  80

<210> SEQ ID NO 35
<211> LENGTH: 79
<212> TYPE: PRT
<213> ORGANISM: ARTIFICIAL
<220> FEATURE:
<223> OTHER INFORMATION: Sequence is synthesized

<400> SEQUENCE: 35

Gln Val Gln Leu Gln Glu Ser Gly Pro Gly Leu Val Lys Pro Ser Gln
1               5                   10                  15

Thr Leu Ser Leu Thr Cys Thr Val Ser Trp Ile Arg Gln Pro Pro Gly
            20                  25                  30

Lys Gly Leu Glu Trp Ile Arg Val Thr Ile Ser Val Asp Thr Ser Lys
        35                  40                  45

Asn Gln Phe Ser Leu Lys Leu Ser Ser Val Thr Ala Ala Asp Thr Ala
    50                  55                  60

Val Tyr Tyr Cys Trp Gly Gln Gly Thr Leu Val Thr Val Ser Ser
65                  70                  75

<210> SEQ ID NO 36
<211> LENGTH: 87
<212> TYPE: PRT
<213> ORGANISM: ARTIFICIAL
<220> FEATURE:
<223> OTHER INFORMATION: Sequence is synthesized

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Trp Val
            20                  25                  30

Arg Gln Ala Pro Gly Lys Gly Leu Glu Trp Val Ser Arg Phe Thr Ile
        35                  40                  45

Ser Arg Asp Asn Ser Lys Asn Thr Leu Tyr Leu Gln Met Asn Ser Leu
    50                  55                  60

Arg Ala Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 37
<211> LENGTH: 81
<212> TYPE: PRT
<213> ORGANISM: ARTIFICIAL
<220> FEATURE:
<223> OTHER INFORMATION: Sequence is synthesized
```

```
<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Arg Asp Asn Ser Lys
        35                  40                  45

Asn Thr Leu Tyr Leu Gln Met Asn Ser Leu Arg Ala Glu Asp Thr Ala
    50                  55                  60

Val Tyr Tyr Cys Ala Arg Trp Gly Gln Gly Thr Leu Val Thr Val Ser
65                  70                  75                  80

Ser

<210> SEQ ID NO 38
<211> LENGTH: 80
<212> TYPE: PRT
<213> ORGANISM: ARTIFICIAL
<220> FEATURE:
<223> OTHER INFORMATION: Sequence is synthesized

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Arg Asp Asn Ser Lys
        35                  40                  45

Asn Thr Leu Tyr Leu Gln Met Asn Ser Leu Arg Ala Glu Asp Thr Ala
    50                  55                  60

Val Tyr Tyr Cys Ala Trp Gly Gln Gly Thr Leu Val Thr Val Ser Ser
65                  70                  75                  80

<210> SEQ ID NO 39
<211> LENGTH: 79
<212> TYPE: PRT
<213> ORGANISM: ARTIFICIAL
<220> FEATURE:
<223> OTHER INFORMATION: Sequence is synthesized

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Arg Asp Asn Ser Lys
        35                  40                  45

Asn Thr Leu Tyr Leu Gln Met Asn Ser Leu Arg Ala Glu Asp Thr Ala
    50                  55                  60

Val Tyr Tyr Cys Trp Gly Gln Gly Thr Leu Val Thr Val Ser Ser
65                  70                  75

<210> SEQ ID NO 40
<211> LENGTH: 87
<212> TYPE: PRT
<213> ORGANISM: ARTIFICIAL
<220> FEATURE:
<223> OTHER INFORMATION: Sequence is synthesized

<400> SEQUENCE: 40
```

```
Glu Val Gln Leu Val Glu Ser Gly Gly Gly Leu Val Gln Pro Gly
1               5                   10                  15

Ser Leu Arg Leu Ser Cys Ala Ala Ser Gly Phe Asn Ile Lys Trp Val
            20                  25                  30

Arg Gln Ala Pro Gly Lys Gly Leu Glu Trp Val Ser Arg Phe Thr Ile
        35                  40                  45

Ser Ala Asp Thr Ser Lys Asn Thr Ala Tyr Leu Gln Met Asn Ser Leu
    50                  55                  60

Arg Ala Glu Asp Thr Ala Val Tyr Tyr Cys Ser Arg Trp Gly Gln Gly
65                  70                  75                  80

Thr Leu Val Thr Val Ser Ser
                85
```

<210> SEQ ID NO 41
<211> LENGTH: 81
<212> TYPE: PRT
<213> ORGANISM: ARTIFICIAL
<220> FEATURE:
<223> OTHER INFORMATION: Sequence is synthesized

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
        35                  40                  45

Asn Thr Ala Tyr Leu Gln Met Asn Ser Leu Arg Ala Glu Asp Thr Ala
    50                  55                  60

Val Tyr Tyr Cys Ser Arg Trp Gly Gln Gly Thr Leu Val Thr Val Ser
65                  70                  75                  80

Ser
```

<210> SEQ ID NO 42
<211> LENGTH: 80
<212> TYPE: PRT
<213> ORGANISM: ARTIFICIAL
<220> FEATURE:
<223> OTHER INFORMATION: Sequence is synthesized

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
        35                  40                  45

Asn Thr Ala Tyr Leu Gln Met Asn Ser Leu Arg Ala Glu Asp Thr Ala
    50                  55                  60

Val Tyr Tyr Cys Ser Trp Gly Gln Gly Thr Leu Val Thr Val Ser Ser
65                  70                  75                  80
```

<210> SEQ ID NO 43
<211> LENGTH: 87
<212> TYPE: PRT
<213> ORGANISM: ARTIFICIAL
<220> FEATURE:
<223> OTHER INFORMATION: Sequence is synthesized

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Trp Val
            20                  25                  30

Arg Gln Ala Pro Gly Lys Gly Leu Glu Trp Val Ser Arg Phe Thr Ile
        35                  40                  45

Ser Ala Asp Thr Ser Lys Asn Thr Ala Tyr Leu Gln Met Asn Ser Leu
50                  55                  60

Arg Ala Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 44
<211> LENGTH: 81
<212> TYPE: PRT
<213> ORGANISM: ARTIFICIAL
<220> FEATURE:
<223> OTHER INFORMATION: Sequence is synthesized

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
        35                  40                  45

Asn Thr Ala Tyr Leu Gln Met Asn Ser Leu Arg Ala Glu Asp Thr Ala
    50                  55                  60

Val Tyr Tyr Cys Ala Arg Trp Gly Gln Gly Thr Leu Val Thr Val Ser
65                  70                  75                  80

Ser

<210> SEQ ID NO 45
<211> LENGTH: 80
<212> TYPE: PRT
<213> ORGANISM: ARTIFICIAL
<220> FEATURE:
<223> OTHER INFORMATION: Sequence is synthesized

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
        35                  40                  45

Asn Thr Ala Tyr Leu Gln Met Asn Ser Leu Arg Ala Glu Asp Thr Ala
    50                  55                  60

Val Tyr Tyr Cys Ala Trp Gly Gln Gly Thr Leu Val Thr Val Ser Ser
65                  70                  75                  80

<210> SEQ ID NO 46
<211> LENGTH: 79
<212> TYPE: PRT
<213> ORGANISM: ARTIFICIAL
<220> FEATURE:
<223> OTHER INFORMATION: Sequence is synthesized

<400> SEQUENCE: 46

Glu Val Gln Leu Val Glu Ser Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
        35                  40                  45

Asn Thr Ala Tyr Leu Gln Met Asn Ser Leu Arg Ala Glu Asp Thr Ala
    50                  55                  60

Val Tyr Tyr Cys Trp Gly Gln Gly Thr Leu Val Thr Val Ser Ser
65                  70                  75

<210> SEQ ID NO 47
<211> LENGTH: 80
<212> TYPE: PRT
<213> ORGANISM: ARTIFICIAL
<220> FEATURE:
<223> OTHER INFORMATION: Sequence is synthesized

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
        35                  40                  45

Ser Gly Thr Asp Phe Thr Leu Thr Ile Ser Ser Leu Gln Pro Glu Asp
    50                  55                  60

Phe Ala Thr Tyr Tyr Cys Phe Gly Gln Gly Thr Lys Val Glu Ile Lys
65                  70                  75                  80

<210> SEQ ID NO 48
<211> LENGTH: 80
<212> TYPE: PRT
<213> ORGANISM: ARTIFICIAL
<220> FEATURE:
<223> OTHER INFORMATION: Sequence is synthesized

<400> SEQUENCE: 48

Asp Ile Val Met Thr Gln Ser Pro Leu Ser Leu Pro Val Thr Pro Gly
1               5                   10                  15

Glu Pro Ala Ser Ile Ser Cys Trp Tyr Leu Gln Lys Pro Gly Gln Ser
            20                  25                  30

Pro Gln Leu Leu Ile Tyr Gly Val Pro Asp Arg Phe Ser Gly Ser Gly
        35                  40                  45

Ser Gly Thr Asp Phe Thr Leu Lys Ile Ser Arg Val Glu Ala Glu Asp
    50                  55                  60

Val Gly Val Tyr Tyr Cys Phe Gly Gln Gly Thr Lys Val Glu Ile Lys
65                  70                  75                  80

<210> SEQ ID NO 49
<211> LENGTH: 80
<212> TYPE: PRT
<213> ORGANISM: ARTIFICIAL
<220> FEATURE:
<223> OTHER INFORMATION: Sequence is synthesized

<400> SEQUENCE: 49

Glu Ile Val Leu Thr Gln Ser Pro Gly Thr Leu Ser Leu Ser Pro Gly
1               5                   10                  15

Glu Arg Ala Thr Leu Ser Cys Trp Tyr Gln Gln Lys Pro Gly Gln Ala
            20                  25                  30

```
Pro Arg Leu Leu Ile Tyr Gly Ile Pro Asp Arg Phe Ser Gly Ser Gly
        35                  40                  45

Ser Gly Thr Asp Phe Thr Leu Thr Ile Ser Arg Leu Glu Pro Glu Asp
 50                  55                  60

Phe Ala Val Tyr Tyr Cys Phe Gly Gln Gly Thr Lys Val Glu Ile Lys
 65                  70                  75                  80

<210> SEQ ID NO 50
<211> LENGTH: 80
<212> TYPE: PRT
<213> ORGANISM: ARTIFICIAL
<220> FEATURE:
<223> OTHER INFORMATION: Sequence is synthesized

<400> SEQUENCE: 50

Asp Ile Val Met Thr Gln Ser Pro Asp Ser Leu Ala Val Ser Leu Gly
 1               5                  10                  15

Glu Arg Ala Thr Ile Asn Cys Trp Tyr Gln Gln Lys Pro Gly Gln Pro
             20                  25                  30

Pro Lys Leu Leu Ile Tyr Gly Val Pro Asp Arg Phe Ser Gly Ser Gly
         35                  40                  45

Ser Gly Thr Asp Phe Thr Leu Thr Ile Ser Ser Leu Gln Ala Glu Asp
 50                  55                  60

Val Ala Val Tyr Tyr Cys Phe Gly Gln Gly Thr Lys Val Glu Ile Lys
 65                  70                  75                  80

<210> SEQ ID NO 51
<211> LENGTH: 31
<212> TYPE: PRT
<213> ORGANISM: ARTIFICIAL
<220> FEATURE:
<223> OTHER INFORMATION: Sequence is synthesized

<400> SEQUENCE: 51

Arg Phe Val Phe Ser Leu Asp Thr Ser Val Ser Thr Ala Tyr Leu Gln
 1               5                  10                  15

Ile Ser Ser Leu Lys Ala Glu Asp Thr Ala Val Tyr Tyr Cys Ser
             20                  25                  30

<210> SEQ ID NO 52
<211> LENGTH: 32
<212> TYPE: PRT
<213> ORGANISM: ARTIFICIAL
<220> FEATURE:
<223> OTHER INFORMATION: Sequence is synthesized

<400> SEQUENCE: 52

Arg Phe Val Phe Ser Leu Asp Thr Ser Val Ser Thr Ala Tyr Leu Gln
 1               5                  10                  15

Ile Ser Ser Leu Lys Ala Glu Asp Thr Ala Val Tyr Tyr Cys Ser Arg
             20                  25                  30

<210> SEQ ID NO 53
<211> LENGTH: 10
<212> TYPE: PRT
<213> ORGANISM: ARTIFICIAL
<220> FEATURE:
<223> OTHER INFORMATION: Sequence is synthesized

<400> SEQUENCE: 53

Phe Gly Gln Gly Thr Lys Val Glu Ile Lys
 1               5                  10
```

```
<210> SEQ ID NO 54
<211> LENGTH: 10
<212> TYPE: PRT
<213> ORGANISM: ARTIFICIAL
<220> FEATURE:
<223> OTHER INFORMATION: Sequence is synthesized
<220> FEATURE:
<221> NAME/KEY: misc_feature
<222> LOCATION: (7)..(7)
<223> OTHER INFORMATION: Xaa can be any naturally occurring amino acid

<400> SEQUENCE: 54

Phe Gly Gln Gly Thr Lys Xaa Glu Ile Lys
1               5                   10

<210> SEQ ID NO 55
<211> LENGTH: 87
<212> TYPE: PRT
<213> ORGANISM: ARTIFICIAL
<220> FEATURE:
<223> OTHER INFORMATION: Sequence is synthesized

<400> SEQUENCE: 55

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Trp Val
            20                  25                  30

Arg Gln Ala Pro Gly Gln Gly Leu Glu Trp Met Gly Arg Phe Val Phe
        35                  40                  45

Ser Leu Asp Thr Ser Val Ser Thr Ala Tyr Leu Gln Ile Ser Ser Leu
    50                  55                  60

Lys Ala Glu Asp Thr Ala Val Tyr Tyr Cys Ala Arg Trp Gly Gln Gly
65                  70                  75                  80

Thr Ser Leu Thr Val Ser Ser
                85

<210> SEQ ID NO 56
<211> LENGTH: 81
<212> TYPE: PRT
<213> ORGANISM: artificial
<220> FEATURE:
<223> OTHER INFORMATION: Sequence is synthesized

<400> SEQUENCE: 56

Gln Val Gln Leu Val Gln Ser Gly Ser Glu Leu Lys Lys Pro Gly Ala
1               5                   10                  15

Ser Val Lys Val Ser Cys Lys Ala Ser Trp Val Arg Gln Ala Pro Gly
            20                  25                  30

Gln Gly Leu Glu Trp Met Arg Phe Val Phe Ser Leu Asp Thr Ser Val
        35                  40                  45

Ser Thr Ala Tyr Leu Gln Ile Ser Ser Leu Lys Ala Glu Asp Thr Ala
    50                  55                  60

Val Tyr Tyr Cys Ala Arg Trp Gly Gln Gly Thr Ser Leu Thr Val Ser
65                  70                  75                  80

Ser

<210> SEQ ID NO 57
<211> LENGTH: 80
<212> TYPE: PRT
<213> ORGANISM: artificial
<220> FEATURE:
<223> OTHER INFORMATION: Sequence is synthesized
```

```
<400> SEQUENCE: 57

Gln Val Gln Leu Val Gln Ser Gly Ser Glu Leu Lys Lys Pro Gly Ala
1               5                   10                  15

Ser Val Lys Val Ser Cys Lys Ala Ser Trp Val Arg Gln Ala Pro Gly
                20                  25                  30

Gln Gly Leu Glu Trp Met Arg Phe Val Phe Ser Leu Asp Thr Ser Val
            35                  40                  45

Ser Thr Ala Tyr Leu Gln Ile Ser Ser Leu Lys Ala Glu Asp Thr Ala
        50                  55                  60

Val Tyr Tyr Cys Ala Trp Gly Gln Gly Thr Ser Leu Thr Val Ser Ser
65                  70                  75                  80

<210> SEQ ID NO 58
<211> LENGTH: 79
<212> TYPE: PRT
<213> ORGANISM: ARTIFICIAL
<220> FEATURE:
<223> OTHER INFORMATION: Sequence is synthesized

<400> SEQUENCE: 58

Gln Val Gln Leu Val Gln Ser Gly Ser Glu Leu Lys Lys Pro Gly Ala
1               5                   10                  15

Ser Val Lys Val Ser Cys Lys Ala Ser Trp Val Arg Gln Ala Pro Gly
                20                  25                  30

Gln Gly Leu Glu Trp Met Arg Phe Val Phe Ser Leu Asp Thr Ser Val
            35                  40                  45

Ser Thr Ala Tyr Leu Gln Ile Ser Ser Leu Lys Ala Glu Asp Thr Ala
        50                  55                  60

Val Tyr Tyr Cys Trp Gly Gln Gly Thr Ser Leu Thr Val Ser Ser
65                  70                  75
```